(12) United States Patent
Yeh et al.

(10) Patent No.: US 12,221,613 B2
(45) Date of Patent: Feb. 11, 2025

(54) APPROACHES TO DRAMATICALLY INCREASE RICE PRODUCTIVITY

(71) Applicant: Academia Sinica, Taipei (TW)

(72) Inventors: Su-Ying Yeh, Chiayi (TW); Hsin-Hung Lin, Taipei (TW); Maurice S. B. Ku, Kaohsing (TW); Wen-Hsiung Li, Yuanshan Township (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 17/923,455

(22) PCT Filed: Apr. 29, 2021

(86) PCT No.: PCT/US2021/029863
§ 371 (c)(1),
(2) Date: Nov. 4, 2022

(87) PCT Pub. No.: WO2021/225862
PCT Pub. Date: Nov. 11, 2021

(65) Prior Publication Data
US 2023/0203521 A1    Jun. 29, 2023

Related U.S. Application Data

(60) Provisional application No. 63/019,672, filed on May 4, 2020.

(51) Int. Cl.
C12N 15/82    (2006.01)
(52) U.S. Cl.
CPC ..... *C12N 15/8269* (2013.01); *C12N 15/8265* (2013.01)
(58) Field of Classification Search
CPC ............ C12N 15/8269; C12N 15/8265; C12N 15/8261; Y02A 40/146; A01H 5/10; C07K 14/415
See application file for complete search history.

(56) References Cited

U.S. PATENT DOCUMENTS

2008/0148432 A1* 6/2008 Abad ................. C12N 15/8247
  435/468
2009/0241218 A1* 9/2009 Frankard ............. C07K 14/415
  800/278

OTHER PUBLICATIONS

Wu, Jingrui, et al. "Overexpression of zmm28 increases maize grain yield in the field." Proceedings of the National Academy of Sciences 116.47 (2019): 23850-23858. (Year: 2019).*
Gen Bank Accession No. AC205063 "*Zea mays* cultivar B73 chromosome 9 clone CH201-98K18" dated Sep. 13, 2014 [online]. Retrieved on Nov. 14, 2023 from the internet at https://www.ncbi.nlm.nih.gov/nuccore/AC205063. Entire document; sequence residues 57271-55138. (Year: 2014).*
Gen Bank Accession No. AC155363 "*Zea mays* strain B73 clone ZMMBBb0049G20" dated Jan. 25, 2005 [online]. Retrieved on Nov. 14, 2023 from the internet at https://www.ncbi.nlm.nih.gov/nuccore/AC155363. Entire document; sequence residues 21708-23649. (Year: 2005).*
Gen Bank Accession No. AF318580 "*Zea mays* putative transcription factor ZmGLK1 (Glk1) mRNA, complete cds" dated May 8, 2001 [online]. Retrieved on Nov. 14, 2023 from the internet at https://www.ncbi.nlm.nih.gov/nuccore/AF318580. Entire document; sequence residues 163-1590. (Year: 2001).*
GenBank Accession No. AF318579 "*Zea mays* putative transcription factor GOLDEN 2 mRNA, complete cds" dated May 8, 2001 [online]. Retrieved on Nov. 14, 2023 from the internet at https://www.ncbi.nlm.nih.gov/nuccore/AF318579. Entire document; sequence residues 412-1797. (Year: 2001).*
Streatfield, Stephen J et al. "Analysis of the maize polyubiquitin-1 promoter heat shock elements and generation of promoter variants with modified expression characteristics." Transgenic research vol. 13,4 (2004): 299-312. doi: 10.1023/b:trag.0000040053.23687.9c (Year: 2004).*
Fitter, David W., et al. "GLK gene pairs regulate chloroplast development in diverse plant species." The Plant Journal 31.6 (2002): 713-727. (Year: 2002).*
Powell, Ann LT, et al. "Uniform ripening encodes a Golden 2-like transcription factor regulating tomato fruit chloroplast development." Science 336.6089 (2012): 1711-1715. (Year: 2012).*
Brand, Arnon, et al. "CaGLK2 regulates natural variation of chlorophyll content and fruit color in pepper fruit." Theoretical and Applied Genetics 127 (2014): 2139-2148. (Year: 2014).*
Li, Guangwei, et al. "Heterologous expression of kiwifruit (*Actinidia chinensis*) GOLDEN2-LIKE homolog elevates chloroplast level and nutritional quality in tomato (*Solanum lycopersicum*)." Planta 247 (2018): 1351-1362. (Year: 2018).*
Nagatoshi, Yukari, et al. "GOLDEN 2-LIKE transcription factors for chloroplast development affect ozone tolerance through the regulation of stomatal movement." Proceedings of the National Academy of Sciences 113.15 (2016): 4218-4223. (Year: 2016).*

(Continued)

*Primary Examiner* — Charles Logsdon
*Assistant Examiner* — Kelsey L McWilliams
(74) *Attorney, Agent, or Firm* — Morse, Barnes-Brown & Pendleton, P.C.; Russell L. Widom

(57) ABSTRACT

A transgenic rice plant containing in its genome a recombinant DNA construct that includes a first nucleic acid having a sequence of a first Golden 2-like transcription factor (GLK) gene operably linked to its natural promoter and 5' untranslated region (5'UTR), and a second nucleic acid having a sequence of a second GLK gene operably linked to its natural promoter and 5'UTR, the second GLK gene being distinct from the first GLK gene. The first GLK gene and the second GLK gene are both from a C4 plant and the transgenic rice plant exhibits a 65-106% increase in shoot biomass and a 50-95% increase in grain yield, as compared to an untransformed wild-type rice plant. Also provided is a method for producing the transgenic rice plant and a recombinant DNA construct that can be used in the method.

15 Claims, 8 Drawing Sheets
Specification includes a Sequence Listing.

(56) References Cited

OTHER PUBLICATIONS

Ahmad—GOLDEN2-LIKE Transcription Factors Regulate WRKY40 Expression in Response to Abscisic Acid; *Plant Physiology*, Apr. 2019, vol. 179, pp. 1844-1860.
Fitter, et al.—"GLK Gene Pairs Regulate Chloroplast Development in Diverse Plant Species", *The Plant Journal*, 31(6), pp. 713-727.
GenBank Accession No. AC205063 "*Zea mays* cultivar B73 chromosome 9 clone CH201-98K18" dated Sep. 13, 2014 [online]. Retrieved on Aug. 10, 2021 from the internet at https://www.ncbi.nlm.nih.gov/nuccore/AC205063. Entire document; sequence residues 57271-55138.
GenBank Accession No. AC155363 "*Zea mays* strain B73 clone ZMMBBb0049G20" dated Jan. 25, 2005 [online]. Retrieved on Aug. 10, 2021 from the internet at https://www.ncbi.nlm.nih.gov/nuccore/AC155363. Entire document; sequence residues 21708-23649.
GenBank Accession No. AF318580 "*Zea mays* putative transcription factor ZmGLK1 (Glk1) mRNA, complete cds" dated May 8, 2001 [online]. Retrieved on Aug. 10, 2021 from the internet at https://www.ncbi.nlm.nih.gov/nuccore/AF318580. Entire document; sequence residues 163-1590.
GenBank Accession No. AF318579 "*Zea mays* putative transcription factor GOLDEN 2 mRNA, complete cds" dated May 8, 2001 [online]. Retrieved on Aug. 10, 2021 from the internet at https://www.ncbi.nlm.nih.gov/nuccore/AF318579. Entire document; sequence residues 412-1797.
Gotoh et al.—"Chloroplast Accumulation Response Enhances Leaf Photosynthesis and Plant Biomass Production", *Plant Physiology*, vol. 178, pp. 1358-1369, Nov. 2018.
Han et al.—"GOLDEN2-LIKE transcription factors coordinate the tolerance to Cucumber mosaic virus in *Arabidopsis*", *Biochemical and Biophysical Research Communications*, 477 (2016) 626-632, 2016.
Liu et al.—"AhGLK1 affects chlorophyll biosynthesis and photosynthesis in peanut leaves during recovery from drought", *Scientific Reports*, 11 pages, Feb. 2, 2018.
Nakamura et al.—"Ectopic Overexpression of The Transcription Factor OsGLK1 Induces Chloroplast Development in Non-Green Rice Cells", *Plant Cell Physiol.* 50(11): 1933-1949 (2009).
Nguyen et al.—"Tomato GOLDEN2-LIKE Transcription Factors Reveal Development and Ripening", *The Plant Cell*, vol. 26: 585-601, Feb. 2014.
PCT International Search Report International Application No. PCT/US2021/029863, mailed Oct. 15, 2021, 5 pages.
Powell et al.—"Uniform ripening Encodes a Golden 2-like Transcription Factor Regulating Tomato Fruit Chloroplast Development," *Science* vol. 336, pp. 1711-1715, Jun. 29, 2012.
Rossini et al. "The Maize Golden2 Gene Defines a Novel Class of Transcriptional Regulators in Plants", *The Plant Cell*, vol. 13, 1231-1244, May 2001, 15 pages.
Sakuraba—"Rice Phytochrome-Interacting Factor-Like1 (OsPIL1) is involved in the promotion of chlorophyll biosynthesis through feed-forward regulatory loops", *Journal of Experimental Botany*, vol. 68, No. 15 pp. 4103-4114, 2017.
Wang et al.—"Re-creation of a Key Step in the Evolutionary Switch from Cs to C4 Leaf Anatomy", Current Biology, vol. 27, 2017, 15 pages.
Wang et al.—"Re-creation of a Key Step in the Evolutionary Switch from C3 to C4 Leaf Anatomy", *Current Biology*, Nov. 6, 2017, 17 pages.
Waters et al.—"GLK Transcription Factors Coordinate Expression of the Photosynthetic Apparatus in *Arabidopsis*.", *The Plant Cell*, vol. 21: 1109-1128, Apr. 2009.
Zhu et al.—"Important photosynthetic contribution of silique wall to seed yield related traits in *Arabidopsis thaliana*", Springer Nature B.V., 9 pages, Jun. 29, 2018.

\* cited by examiner

| Up-regulated genes in root | | | |
|---|---|---|---|
| pZmG1::ZmG1 | pZmG2::ZmG2 | pZmG1::ZmG1/pZmG2::ZmG2 | GO biological process |
| ■ | ■ | ■ | jasmonic acid mediated signaling pathway |
| ■ | ■ | ■ | regulation of defense response |
| ■ | ■ | ■ | regulation of response to stress |
| ■ | ■ | ■ | response to wounding |
|  | ■ | ■ | carboxylic acid metabolic process |
|  | ■ | ■ | cellular amide metabolic process |
|  | ■ | ■ | cellular nitrogen compound metabolic process |
|  | ■ | ■ | cellular response to chemical stimulus |
|  | ■ | ■ | cellular response to stimulus |
|  | ■ | ■ | drug metabolic process |
|  | ■ | ■ | glutathione metabolic process |
|  | ■ | ■ | nitrogen compound metabolic process |
|  | ■ | ■ | organic acid metabolic process |
|  | ■ | ■ | oxoacid metabolic process |
|  | ■ | ■ | peptide metabolic process |
|  | ■ | ■ | response to chemical |
|  | ■ | ■ | response to temperature stimulus |
|  | ■ | ■ | response to toxic substance |
|  | ■ | ■ | defense response |
|  | ■ | ■ | hormone biosynthetic process |
|  | ■ | ■ | hormone metabolic process |
|  | ■ | ■ | hormone-mediated signaling pathway |
|  | ■ | ■ | monocarboxylic acid metabolic process |
|  | ■ | ■ | multi-organism process |
|  | ■ | ■ | regulation of hormone levels |
|  | ■ | ■ | regulation of response to stimulus |
|  | ■ | ■ | regulation of signal transduction |
|  | ■ | ■ | regulation of signaling |
|  | ■ | ■ | response to abscisic acid |
|  | ■ | ■ | response to fungus |
|  | ■ | ■ | response to other organism |
|  | ■ | ■ | response to stimulus |
|  |  | ■ | cellular response to lipid |
|  |  | ■ | defense response to other organism |
|  |  | ■ | generation of precursor metabolites and energy |
|  |  | ■ | photosynthesis |
|  |  | ■ | response to abiotic stimulus |
|  |  | ■ | response to acid chemical |
|  |  | ■ | response to light stimulus |
|  |  | ■ | response to lipid |
|  |  | ■ | response to radiation |
|  |  | ■ | response to stress |
|  |  | ■ | signal transduction |

| Down-regulated genes in root | | | |
|---|---|---|---|
| pZmG1::ZmG1 | pZmG2::ZmG2 | pZmG1::ZmG1/pZmG2::ZmG2 | GO biological process |
|  | ■ |  | cation transmembrane transport |
|  | ■ |  | cation transport |
|  | ■ |  | divalent metal ion transport |
|  | ■ |  | inorganic cation transmembrane transport |
|  | ■ |  | ion transmembrane transport |
|  | ■ |  | metal ion transport |
|  | ■ |  | response to iron ion |
|  | ■ |  | transition metal ion transport |
|  | ■ |  | transmembrane transport |
|  | ■ | ■ | response to inorganic substance |
|  |  | ■ | cellular response to chemical stimulus |
|  |  | ■ | cellular response to stimulus |
|  |  | ■ | response to chemical |
|  |  | ■ | response to nitrogen compound |

Fig. 6B

SEQUENCE LISTING

```
<160> NUMBER OF SEQ ID NOS: 63

<210> SEQ ID NO 1
<211> LENGTH: 2134
<212> TYPE: DNA
<213> ORGANISM: Zea mays
<220> FEATURE:
<221> NAME/KEY: promoter
<222> LOCATION: (1)..(1972)
<223> OTHER INFORMATION: ZMG1
<220> FEATURE:
<221> NAME/KEY: 5'UTR
<222> LOCATION: (1973)..(2134)
<223> OTHER INFORMATION: ZMG1

<400> SEQUENCE: 1
ccaaccgctg catatcttgc acgcggaccg acgacatccg cgacacgcca aaatcaacaa      60
aatcgccggc gcgcaactcc tccgccatca aactactcag cgtctcctca gacgaggcgt     120
cggccgacgg tgaggcggcg gccggcggcg tagcggcagc ggaagaagag gaggtcggca     180
tcgctatgta ccgtcggcgg cggcgggcgg tctgcttcac tcgagccaga tctccggcga     240
acaagagcac ggcgggcaga cgagcagcaa ggcggtgaaa aaggcggcta gggttttcac     300
ggagcgcgga aagtgaagtt caaaaaccgc cgacccccgc cccctttat agacagggcg     360 cggctcttcg ggaaacccgc aatccaacag ggcgcggcgc ttcgggaaac ccgcaatcca     420
atagtacgct gtcaatcaac ggtcatgtca aaaaccccg cggaaccact tcgagcgagg     480
gccgcgtctc cgccatctag cgacgtcttc ggcaccaggt gactttgtcg aactggtccc     540
tcggagggca aatgttgggg cgaaggcaaa gacgccaccc ttcgctcgag gccttcgctg     600
cagtcgctgg tctgacagag acaaaacggg cagggacacc cttcgctcga ctcggcacca     660
gacgaaggcc tgcgacggcg tcatcccaca gtgcggcctc gtccagctca gaggcccacg     720
tgtgatccgg cccagtgtaa cgggccctgc gtggccgccg cgtgttacgg gcctaatttg     780
taaaggcatc cctgtaatta cagtctgtaa ccctgcttta tgggaatatt ctggggataa     840
cctaggtagc tcagggcaca tgcgtcctta gcacaaggcg ctgggcgctc aggtacctat     900 aaatacccctc gcacagtgac cgtgggaggc cagattaaca gagctattgc catctagcgc     960
gtaaccctat taacgtcact gttcaccatt gttggccccc cttgcgagtg agagcaagtc    1020
ccaacattat acatcactct tgtagtttca taaactacaa gagagacata taagttttat    1080
aaataaattt acttttattt ttcctataaa gaaataacca aaacaaaaat atacatctcg    1140
atgagttata caactttata gttgaaaact tttacagctc aattattttt tcttcaaaat    1200
```

-continued

```
ttgatttgca tagtgtaaaa aaaacattca gcgaatgatt tctctagctg tttgccgagt    1260
gttaaaaaac actcgccaaa atgtttcttt gctgagtgtt ttttagtcga gcgttttttg    1320
tttgacaatt agtaaagagt ttttttttttg ttttgttgac tgtggaaaga aaacaataa    1380 gcaaattatt taacgctcgg caaagggcca gaattgtgaa ctatatatac tgctccgtct    1440
cgaactaggc catcggagct tctgcgagac actgagaatc cacgaatcca gcagcctcca    1500
tgcatgacct ccaagctcaa cgcagacgtg aagttcaggg cagcactcca cgatgtcccg    1560
ttggggaaga cctaatagga ccgccagtag aaaacgtcac tgtactagta cagtctccag    1620
ccgatataca tgcagctgag ccgctgtcat atcttgttct cttcctgttg ttcgccaccg    1680
tctcacgaga tcgagtccac ctctctgccc agagttgcat caacgaaaag aaaaaggaaa    1740
aaaaaccggc ggttccaaaa aagactcggc cacacacagg cacacgctcg ctacgaggcc    1800
acaataattc gcagaagcga ccaagctgca cttgcgctcg cggacaaggc cacccatcta    1860
aaggattcag agagatcttt gcgaggcttg tggtcgagat gccttcgccg ttcgccacaa    1920
atactccccg gagagcgagt acttactggc tcgccatatg gcaccaacag caaaacagcg    1980
aaacagtgca gagacaagct acaacaacct accctaacag gccattcctt ccactgcact    2040
tcattcgatc ctgagctata gctggctgcc tgagctcgct ccaagaagtg tatctatagt    2100
atagacacta ggcttcgtgt ggcgtgctcg agat    2134
```

<210> SEQ ID NO 2
<211> LENGTH: 1428
<212> TYPE: DNA
<213> ORGANISM: Zea mays
<220> FEATURE:
<221> NAME/KEY: CDS
<222> LOCATION: (1)..(1428)
<223> OTHER INFORMATION: ZMG1

<400> SEQUENCE: 2

```
atg ctt gca gtg tcg ccg tcg ccg gtg cgg tgt gcc gat gcg gag gag      48
Met Leu Ala Val Ser Pro Ser Pro Val Arg Cys Ala Asp Ala Glu Glu
1               5                   10                  15 tgc ggc gga gga ggc gcc agc aag gaa atg gag gag acc gcc gtc ggg      96
Cys Gly Gly Gly Gly Ala Ser Lys Glu Met Glu Glu Thr Ala Val Gly
            20                  25                  30 cct gtg tcc gac tcg gac ctg gat ttc gac ttc acg gtc gac gac ata     144
Pro Val Ser Asp Ser Asp Leu Asp Phe Asp Phe Thr Val Asp Asp Ile
        35                  40                  45 gac ttc ggg gac ttc ttc ctc agg cta gac gac ggg gat gac gcg ctg     192
Asp Phe Gly Asp Phe Phe Leu Arg Leu Asp Asp Gly Asp Asp Ala Leu
    50                  55                  60 ccg ggc ctc gag gtc gac cct gcc gag atc gtc ttc gct gac ttc gag     240
Pro Gly Leu Glu Val Asp Pro Ala Glu Ile Val Phe Ala Asp Phe Glu
65                  70                  75                  80 gca atc gcc acc gcc ggc ggc gat ggc ggc gtc acg gac cag gag gtg     288
Ala Ile Ala Thr Ala Gly Gly Asp Gly Gly Val Thr Asp Gln Glu Val
                85                  90                  95 ccc agt gtc ctg ccc ttt gcg gac gcg gcg cac ata ggc gcc gtg gat     336
Pro Ser Val Leu Pro Phe Ala Asp Ala Ala His Ile Gly Ala Val Asp
            100                 105                 110 ccg tgt tgt ggt gtc ctt ggc gag gac aac gac gca gcg tgc gca gac     384
Pro Cys Cys Gly Val Leu Gly Glu Asp Asn Asp Ala Ala Cys Ala Asp
        115                 120                 125 gtg gaa gaa ggg aaa ggg gag tgc gac cat gcc gac gag gta gca gcc     432
Val Glu Glu Gly Lys Gly Glu Cys Asp His Ala Asp Glu Val Ala Ala
    130                 135                 140
```

```
gcc ggt aat aat aat agc gac tcc ggt gag gcc ggc tgt gga gga gcc      480
Ala Gly Asn Asn Asn Ser Asp Ser Gly Glu Ala Gly Cys Gly Gly Ala
145                 150                 155                 160 ttt gcc ggc gaa aaa tca ccg tcg tcg acg gca tcg tcg tcg cag gag      528
Phe Ala Gly Glu Lys Ser Pro Ser Ser Thr Ala Ser Ser Ser Gln Glu
                165                 170                 175 gct gag agc cgg cgc aag gtg tcc aag aag cac tcc caa ggg aag aag      576
Ala Glu Ser Arg Arg Lys Val Ser Lys Lys His Ser Gln Gly Lys Lys
            180                 185                 190 aaa gca aag gtg gat tgg acg ccg gag ctt cac cgg aga ttc gtt cag      624
Lys Ala Lys Val Asp Trp Thr Pro Glu Leu His Arg Arg Phe Val Gln
        195                 200                 205 gcg gtg gag gag ctg ggc atc gac aag gcg gtg ccc tcc agg atc ctc      672
Ala Val Glu Glu Leu Gly Ile Asp Lys Ala Val Pro Ser Arg Ile Leu
    210                 215                 220 gag atc atg ggg atc gac tcc ctc acg cgg cat aac ata gcc agc cat      720
Glu Ile Met Gly Ile Asp Ser Leu Thr Arg His Asn Ile Ala Ser His
225                 230                 235                 240 ctg cag aag tac cgt tcc cac agg aag cac atg ctt gcg agg gag gtg      768
Leu Gln Lys Tyr Arg Ser His Arg Lys His Met Leu Ala Arg Glu Val
                245                 250                 255 gag gca gcg acg tgg acg acg cac cgg cgg ccg atg tac gct gcc ccc      816
Glu Ala Ala Thr Trp Thr Thr His Arg Arg Pro Met Tyr Ala Ala Pro
            260                 265                 270 agc ggc gcc gtg aag agg ccc gac tct aac gcg tgg acc gtg ccg acc      864
Ser Gly Ala Val Lys Arg Pro Asp Ser Asn Ala Trp Thr Val Pro Thr
        275                 280                 285 atc ggt ttc cct ccg ccg gcg ggg acc cct cct cgt ccg gtg cag cac      912
Ile Gly Phe Pro Pro Pro Ala Gly Thr Pro Pro Arg Pro Val Gln His
    290                 295                 300 ttc ggg agg cca ctg cac gtc tgg ggc cat ccg agt ccg acg cca gcg      960
Phe Gly Arg Pro Leu His Val Trp Gly His Pro Ser Pro Thr Pro Ala
305                 310                 315                 320 gtg gag tca ccc cgg gtg cca atg tgg cct cgg cat ctc gcc ccc cgc     1008
Val Glu Ser Pro Arg Val Pro Met Trp Pro Arg His Leu Ala Pro Arg
                325                 330                 335 gcc ccg ccg ccg ccg ccg tgg gct ccg cca ccg gct gac ccg gcg          1056
Ala Pro Pro Pro Pro Pro Trp Ala Pro Pro Pro Ala Asp Pro Ala
            340                 345                 350 tcg ttc tgg cac cat gct tac atg agg ggg cct gct gcc cat atg cca     1104
Ser Phe Trp His His Ala Tyr Met Arg Gly Pro Ala Ala His Met Pro
        355                 360                 365 gac cag gtg gcg gtg act cca tgc gtg gca gtg cca atg gca gca gcg     1152
Asp Gln Val Ala Val Thr Pro Cys Val Ala Val Pro Met Ala Ala Ala
    370                 375                 380 cgt ttc cct gct cca cac gtg agg ggt tct ttg cca tgg cca cct ccg     1200
Arg Phe Pro Ala Pro His Val Arg Gly Ser Leu Pro Trp Pro Pro Pro
385                 390                 395                 400 atg tac aga cct ctc gtt cct cca gca ctc gca ggc aag agc cag caa     1248
Met Tyr Arg Pro Leu Val Pro Pro Ala Leu Ala Gly Lys Ser Gln Gln
                405                 410                 415 gac gcg ctg ttt cag cta cag ata cag cca tca agc gag agc ata gat     1296
Asp Ala Leu Phe Gln Leu Gln Ile Gln Pro Ser Ser Glu Ser Ile Asp
            420                 425                 430 gca gca ata ggt gat gtc tta acg aag ccg tgg ctg ccg ctg ccc ctc     1344
Ala Ala Ile Gly Asp Val Leu Thr Lys Pro Trp Leu Pro Leu Pro Leu
        435                 440                 445 gga ctg aag ccc cct tcg gta gac agt gtc atg ggc gag ctg cag agg     1392
Gly Leu Lys Pro Pro Ser Val Asp Ser Val Met Gly Glu Leu Gln Arg
```

```
            450             455             460
caa ggc gta gcg aat gtg ccg caa gct tgt gga tga                        1428
Gln Gly Val Ala Asn Val Pro Gln Ala Cys Gly
465                 470             475
```

<210> SEQ ID NO 3
<211> LENGTH: 475
<212> TYPE: PRT
<213> ORGANISM: Zea mays

<400> SEQUENCE: 3

```
Met Leu Ala Val Ser Pro Ser Pro Val Arg Cys Ala Asp Ala Glu Glu
1               5                   10                  15

Cys Gly Gly Gly Ala Ser Lys Glu Met Glu Thr Ala Val Gly
                20                  25                  30

Pro Val Ser Asp Ser Asp Leu Asp Phe Asp Phe Thr Val Asp Asp Ile
            35                  40                  45

Asp Phe Gly Asp Phe Leu Arg Leu Asp Asp Gly Asp Asp Ala Leu
50                  55                  60

Pro Gly Leu Glu Val Asp Pro Ala Glu Ile Val Phe Ala Asp Phe Glu
65                  70                  75                  80

Ala Ile Ala Thr Ala Gly Gly Asp Gly Gly Val Thr Asp Gln Glu Val
                85                  90                  95

Pro Ser Val Leu Pro Phe Ala Asp Ala Ala His Ile Gly Ala Val Asp
            100                 105                 110

Pro Cys Cys Gly Val Leu Gly Glu Asp Asn Asp Ala Ala Cys Ala Asp
        115                 120                 125

Val Glu Glu Gly Lys Gly Glu Cys Asp His Ala Asp Glu Val Ala Ala
130                 135                 140

Ala Gly Asn Asn Asn Ser Asp Ser Gly Glu Ala Gly Cys Gly Gly Ala
145                 150                 155                 160

Phe Ala Gly Glu Lys Ser Pro Ser Ser Thr Ala Ser Ser Ser Gln Glu
                165                 170                 175

Ala Glu Ser Arg Arg Lys Val Ser Lys Lys His Ser Gln Gly Lys Lys
            180                 185                 190

Lys Ala Lys Val Asp Trp Thr Pro Glu Leu His Arg Arg Phe Val Gln
        195                 200                 205

Ala Val Glu Glu Leu Gly Ile Asp Lys Ala Val Pro Ser Arg Ile Leu
210                 215                 220

Glu Ile Met Gly Ile Asp Ser Leu Thr Arg His Asn Ile Ala Ser His
225                 230                 235                 240

Leu Gln Lys Tyr Arg Ser His Arg Lys His Met Leu Ala Arg Glu Val
                245                 250                 255

Glu Ala Ala Thr Trp Thr Thr His Arg Arg Pro Met Tyr Ala Ala Pro
            260                 265                 270

Ser Gly Ala Val Lys Arg Pro Asp Ser Asn Ala Trp Thr Val Pro Thr
        275                 280                 285

Ile Gly Phe Pro Pro Ala Gly Thr Pro Arg Pro Val Gln His
290                 295                 300

Phe Gly Arg Pro Leu His Val Trp Gly His Pro Ser Pro Thr Pro Ala
305                 310                 315                 320

Val Glu Ser Pro Arg Val Pro Met Trp Pro Arg His Leu Ala Pro Arg
                325                 330                 335

Ala Pro Pro Pro Pro Trp Ala Pro Pro Ala Asp Pro Ala
            340                 345                 350
```

Ser Phe Trp His His Ala Tyr Met Arg Gly Pro Ala Ala His Met Pro
    355                 360                 365

Asp Gln Val Ala Val Thr Pro Cys Val Ala Val Pro Met Ala Ala Ala
    370                 375                 380

Arg Phe Pro Ala Pro His Val Arg Gly Ser Leu Pro Trp Pro Pro
385                 390                 395                 400

Met Tyr Arg Pro Leu Val Pro Pro Ala Leu Ala Gly Lys Ser Gln Gln
                405                 410                 415

Asp Ala Leu Phe Gln Leu Gln Ile Gln Pro Ser Ser Glu Ser Ile Asp
                420                 425                 430

Ala Ala Ile Gly Asp Val Leu Thr Lys Pro Trp Leu Pro Leu Pro Leu
                435                 440                 445

Gly Leu Lys Pro Pro Ser Val Asp Ser Val Met Gly Glu Leu Gln Arg
    450                 455                 460

Gln Gly Val Ala Asn Val Pro Gln Ala Cys Gly
465                 470                 475

<210> SEQ ID NO 4
<211> LENGTH: 1942
<212> TYPE: DNA
<213> ORGANISM: Zea mays
<220> FEATURE:
<221> NAME/KEY: promoter
<222> LOCATION: (1)..(1288)
<223> OTHER INFORMATION: ZMG2
<220> FEATURE:
<221> NAME/KEY: 5'UTR
<222> LOCATION: (1289)..(1942)
<223> OTHER INFORMATION: ZMG2

<400> SEQUENCE: 4
aagcttcagg ttattggata aggtgaggaa aattccatat ttctgaaaaa ccgatgatca      60
aagttagtcc aagtgtctag gtcgcggatc gttcgcgata gcatcggacc gtgcaagcaa     120
agacaccgga ctgttcgacg gcatcagaaa tgtcgcctta gttgattcgg ctaacaatgc     180
ggccgatgca gttgattgga gaatgtcttt gattgtatac ctgcataatc caggtgttag     240
gacagacatg atcatttgac agatagattt caagtatgtt ttaatcgatg atgaacttta     300
tcgctgaact tctagtgatg gcttgcttaa ttgcttgggc cctaacgatg ctttattagc     360 tatgacaaa gtaaatgaag gaatttgtgg tactcatcaa tcggctctaa agatgaagtg     420
gctcttaagg tggtctatgg tttattagcc tgatatgata tcgattgttt taaatactag     480
aaagggtgtg aaatatgtca ggagttcggc gatctgcaat tagttctgag ccccgcgtgc     540
ggaccgtccg gtgtgacacg gagaagaccc gctcatgcag cgagatcgcg gaccgtccgc     600
gctcccgcag agagcaccgc caggagatac atccctaatg tttggctcca aatcggagcc     660
aacactaccc tacatgttct aaattacaat gtgttttagt atttttttta ttgtatagtt     720
tttattatat aacttattat aagtagatga atagtaaaat ctgttggaat atgactctaa     780 tttatttat atatttggaa tatgtcttga aatatgcttt catgtacgcc tataaatata     840
gatctttcat gtaacttgta ttctgcggtt gatagttgat ctgtttcctc gtggtcgttt     900
gctcctccat attggaggga atttttcgcat gtaaatcttt gtgtctattt tatttcgtaa     960
caaaatctat agattctaaa aagctaaaac ttattatagt ttagaacgga ggggcagtgg    1020 ataggccg agtggtatgg caccgtaact gtaaataaca tgcatgcatg gagacgacga    1080
cgcatgtaga ttatatatcg tagtgggggtt ccggaacaat atacaaaaaa catatatgcg    1140

```
tgtatttaat tattatttgt ggcggctggt gcatgtgaac tactggaata ataatggtga    1200
aattgaggag ggtgcactga ctgagatacg gtagacatgc atagataagc actgcggagc    1260
catgctgcct gcctgcaata atgcttgtgt gtatacagcg acacgacacg agacgagagg    1320
gagggtgaac tgaaagagag acccggctag agctataaag caagtggggg aagagagaga    1380
gagaggagaa ggagaaggag aggttttttat gtatgtgtgg tggacatgcg tcctcctgtc    1440
gtctcgagag agcggaggcc ctaatactcc aatcaccacg caccaaacta gctagctagc    1500
agtcgtcttg cattgtagct agtccattgc tctcatcttc tcttcttctt cccccagtcc    1560 tcccccctt tccctctc ggcctctctc gctcagctca ctcttcatta agcgagctca       1620
cgtcgttcct cccttcttct tcttcttatc cgttgttcaa ttcgttcagc tagccggcca    1680
gagatcgagc atcatctcca tcatcgattc atccatctca tctttctctt cttctattct    1740
atgtcgtcgt cgtcccagat tagatcgaag ctgctagcag tctatccagt ctctagctag    1800
ctagctagat caagcccgca gactatacaa tataatacaa gctagctacg tgcttattat    1860
tgctttatta gtctagaata atcttgatat atacgatcga acatatatct cgatctccac    1920
cgatacacac ccggccctat cc                                             1942

<210> SEQ ID NO 5
<211> LENGTH: 1386
<212> TYPE: DNA
<213> ORGANISM: Zea mays
<220> FEATURE:
<221> NAME/KEY: CDS
<222> LOCATION: (1)..(1386)
<223> OTHER INFORMATION: ZMG2

<400> SEQUENCE: 5 atg ctt gag gtg tcg acg ctg cgc ggc cct act agc agc ggc agc aag       48
Met Leu Glu Val Ser Thr Leu Arg Gly Pro Thr Ser Ser Gly Ser Lys
1               5                   10                  15 gcg gag cag cac tgc ggc ggc ggc ggc ttc gtc ggc gac cac cat         96
Ala Glu Gln His Cys Gly Gly Gly Gly Phe Val Gly Asp His His
            20                  25                  30 gtg gtg ttc ccg acg tcc ggc gac tgc ttc gcc atg gtg gac gac aac    144
Val Val Phe Pro Thr Ser Gly Asp Cys Phe Ala Met Val Asp Asp Asn
        35                  40                  45 ctc ctg gac tac atc gac ttc agc tgc gac gtg ccc ttc ttc gac gct    192
Leu Leu Asp Tyr Ile Asp Phe Ser Cys Asp Val Pro Phe Phe Asp Ala
50                  55                  60 gac ggg gac atc ctc ccc gac ctg gag gta gac acc acg gag ctc ctc    240
Asp Gly Asp Ile Leu Pro Asp Leu Glu Val Asp Thr Thr Glu Leu Leu
65                  70                  75                  80 gcc gag ttc tcg tcc acc cct cct gcg gac gac ctg ctg gca gtg gca    288
Ala Glu Phe Ser Ser Thr Pro Pro Ala Asp Asp Leu Leu Ala Val Ala
                85                  90                  95 gta ttc ggc gcc gac gac cag ccg gcg gcg gca gta gca caa gag aag    336
Val Phe Gly Ala Asp Asp Gln Pro Ala Ala Ala Val Ala Gln Glu Lys
            100                 105                 110 ccg tcg tcg tcg ttg gag caa aca tgt ggt gac gac aaa ggt gta gca    384
Pro Ser Ser Ser Leu Glu Gln Thr Cys Gly Asp Asp Lys Gly Val Ala
        115                 120                 125 gta gcc gcc gcc aga aga aag ctg cag acg acg acg acg acg acg        432
Val Ala Ala Ala Arg Arg Lys Leu Gln Thr Thr Thr Thr Thr Thr
    130                 135                 140 acg gag gag gag gat tct tct cct gcc ggg tcc ggg gcc aac aag tcg    480
Thr Glu Glu Glu Asp Ser Ser Pro Ala Gly Ser Gly Ala Asn Lys Ser
145                 150                 155                 160
```

```
tcg gcg tcg gca gag ggc cac agc agc aag aag aag tcg gcg ggc aag        528
Ser Ala Ser Ala Glu Gly His Ser Ser Lys Lys Lys Ser Ala Gly Lys
                165                 170                 175 aac tcc aac ggc ggc aag cgc aag gtg aag gtg gac tgg acg ccg gag        576
Asn Ser Asn Gly Gly Lys Arg Lys Val Lys Val Asp Trp Thr Pro Glu
            180                 185                 190 ctg cac cgg cgg ttc gtg cag gcg gtg gag cag ctg ggc atc gac aag        624
Leu His Arg Arg Phe Val Gln Ala Val Glu Gln Leu Gly Ile Asp Lys
        195                 200                 205 gcc gtg ccg tcc agg atc ctg gag atc atg ggc acg gac tgc ctc aca        672
Ala Val Pro Ser Arg Ile Leu Glu Ile Met Gly Thr Asp Cys Leu Thr
    210                 215                 220 agg cac aac att gcc agc cac ctc cag aag tac cgg tcg cac aga aag        720
Arg His Asn Ile Ala Ser His Leu Gln Lys Tyr Arg Ser His Arg Lys
225                 230                 235                 240 cac ctg atg gcg cgg gag gcg gag gcc gcc acc tgg gcg cag aag cgc        768
His Leu Met Ala Arg Glu Ala Glu Ala Ala Thr Trp Ala Gln Lys Arg
                245                 250                 255 cac atg tac gcg ccg cca gct cca agg acg acg acg acg gac gcc            816
His Met Tyr Ala Pro Pro Ala Pro Arg Thr Thr Thr Thr Asp Ala
                260                 265                 270 gcc agg ccg ccg tgg gtg gtg ccg acg acc atc ggg ttc ccg ccg ccg        864
Ala Arg Pro Pro Trp Val Val Pro Thr Thr Ile Gly Phe Pro Pro Pro
        275                 280                 285 cgc ttc tgc cgc ccg ctg cac gtg tgg ggc cac ccg ccg cac gcc            912
Arg Phe Cys Arg Pro Leu His Val Trp Gly His Pro Pro His Ala
    290                 295                 300 gcc gcg gct gaa gca gca gcg gcg act ccc atg ctg ccc gtg tgg ccg        960
Ala Ala Ala Glu Ala Ala Ala Ala Thr Pro Met Leu Pro Val Trp Pro
305                 310                 315                 320 cgt cac ctg gcg ccg ccc cgg cac ctg gcg ccg tgg gcg cac ccg acg       1008
Arg His Leu Ala Pro Pro Arg His Leu Ala Pro Trp Ala His Pro Thr
                325                 330                 335 ccg gtg gac ccg gcg ttc tgg cac cag cag tac agc gct gcc agg aaa       1056
Pro Val Asp Pro Ala Phe Trp His Gln Gln Tyr Ser Ala Ala Arg Lys
                340                 345                 350 tgg ggc cca cag gca gcc gcc gtg acg caa ggg acg cca tgc gtg ccg       1104
Trp Gly Pro Gln Ala Ala Ala Val Thr Gln Gly Thr Pro Cys Val Pro
        355                 360                 365 ctg ccg agg ttt ccg gtg cct cac ccc atc tac agc aga ccg gcg atg       1152
Leu Pro Arg Phe Pro Val Pro His Pro Ile Tyr Ser Arg Pro Ala Met
    370                 375                 380 gta cct ccg ccg cca agc acc acc aag cta gct caa ctg cat ctg gag       1200
Val Pro Pro Pro Pro Ser Thr Thr Lys Leu Ala Gln Leu His Leu Glu
385                 390                 395                 400 ctc caa gcg cac ccg tcc aag gag agc atc gac gca gcc atc gga gat       1248
Leu Gln Ala His Pro Ser Lys Glu Ser Ile Asp Ala Ala Ile Gly Asp
                405                 410                 415 gtt tta gtg aag cca tgg ctg ccg ctt cca ctg ggg ctc aag ccg ccg       1296
Val Leu Val Lys Pro Trp Leu Pro Leu Pro Leu Gly Leu Lys Pro Pro
                420                 425                 430 tcg ctc gac agc gtc atg tcg gag ctg cac aag caa ggc gta cca aaa       1344
Ser Leu Asp Ser Val Met Ser Glu Leu His Lys Gln Gly Val Pro Lys
        435                 440                 445 atc cca ccg gcg gct gcc acc acc acc ggc gcc acc gga tga              1386
Ile Pro Pro Ala Ala Ala Thr Thr Thr Gly Ala Thr Gly
    450                 455                 460
```

<210> SEQ ID NO 6

```
<211> LENGTH: 461
<212> TYPE: PRT
<213> ORGANISM: Zea mays

<400> SEQUENCE: 6
```

| | | | | | | | | | | | | | | |
|---|---|---|---|---|---|---|---|---|---|---|---|---|---|---|
| Met | Leu | Glu | Val | Ser | Thr | Leu | Arg | Gly | Pro | Thr | Ser | Ser | Gly | Ser | Lys |
| 1 | | | | 5 | | | | | 10 | | | | | 15 | |
| Ala | Glu | Gln | His | Cys | Gly | Gly | Gly | Gly | Phe | Val | Gly | Asp | His | His |
| | | | 20 | | | | | 25 | | | | | 30 | |
| Val | Val | Phe | Pro | Thr | Ser | Gly | Asp | Cys | Phe | Ala | Met | Val | Asp | Asp | Asn |
| | | 35 | | | | | 40 | | | | | 45 | | | |
| Leu | Leu | Asp | Tyr | Ile | Asp | Phe | Ser | Cys | Asp | Val | Pro | Phe | Phe | Asp | Ala |
| | 50 | | | | | 55 | | | | | 60 | | | | |
| Asp | Gly | Asp | Ile | Leu | Pro | Asp | Leu | Glu | Val | Asp | Thr | Thr | Glu | Leu | Leu |
| 65 | | | | | 70 | | | | | 75 | | | | | 80 |
| Ala | Glu | Phe | Ser | Ser | Thr | Pro | Pro | Ala | Asp | Asp | Leu | Leu | Ala | Val | Ala |
| | | | | 85 | | | | | 90 | | | | | 95 | |
| Val | Phe | Gly | Ala | Asp | Asp | Gln | Pro | Ala | Ala | Val | Ala | Gln | Glu | Lys |
| | | | 100 | | | | | 105 | | | | | 110 | |
| Pro | Ser | Ser | Ser | Leu | Glu | Gln | Thr | Cys | Gly | Asp | Asp | Lys | Gly | Val | Ala |
| | | 115 | | | | | 120 | | | | | 125 | | | |
| Val | Ala | Ala | Ala | Arg | Arg | Lys | Leu | Gln | Thr | Thr | Thr | Thr | Thr | Thr | Thr |
| | 130 | | | | | 135 | | | | | 140 | | | | |
| Thr | Glu | Glu | Glu | Asp | Ser | Ser | Pro | Ala | Gly | Ser | Gly | Ala | Asn | Lys | Ser |
| 145 | | | | | 150 | | | | | 155 | | | | | 160 |
| Ser | Ala | Ser | Ala | Glu | Gly | His | Ser | Ser | Lys | Lys | Lys | Ser | Ala | Gly | Lys |
| | | | | 165 | | | | | 170 | | | | | 175 | |
| Asn | Ser | Asn | Gly | Gly | Lys | Arg | Lys | Val | Lys | Val | Asp | Trp | Thr | Pro | Glu |
| | | | 180 | | | | | 185 | | | | | 190 | | |
| Leu | His | Arg | Arg | Phe | Val | Gln | Ala | Val | Glu | Gln | Leu | Gly | Ile | Asp | Lys |
| | | | | 195 | | | | | 200 | | | | | 205 | |
| Ala | Val | Pro | Ser | Arg | Ile | Leu | Glu | Ile | Met | Gly | Thr | Asp | Cys | Leu | Thr |
| | 210 | | | | | 215 | | | | | 220 | | | | |
| Arg | His | Asn | Ile | Ala | Ser | His | Leu | Gln | Lys | Tyr | Arg | Ser | His | Arg | Lys |
| 225 | | | | | 230 | | | | | 235 | | | | | 240 |
| His | Leu | Met | Ala | Arg | Glu | Ala | Glu | Ala | Ala | Thr | Trp | Ala | Gln | Lys | Arg |
| | | | | 245 | | | | | 250 | | | | | 255 | |
| His | Met | Tyr | Ala | Pro | Pro | Ala | Pro | Arg | Thr | Thr | Thr | Thr | Thr | Asp | Ala |
| | | | 260 | | | | | 265 | | | | | 270 | | |
| Ala | Arg | Pro | Pro | Trp | Val | Val | Pro | Thr | Thr | Ile | Gly | Phe | Pro | Pro | Pro |
| | | 275 | | | | | 280 | | | | | 285 | | | |
| Arg | Phe | Cys | Arg | Pro | Leu | His | Val | Trp | Gly | His | Pro | Pro | His | Ala |
| | 290 | | | | | 295 | | | | | 300 | | | | |
| Ala | Ala | Ala | Glu | Ala | Ala | Ala | Thr | Pro | Met | Leu | Pro | Val | Trp | Pro |
| 305 | | | | | 310 | | | | | 315 | | | | | 320 |
| Arg | His | Leu | Ala | Pro | Pro | Arg | His | Leu | Ala | Pro | Trp | Ala | His | Pro | Thr |
| | | | | 325 | | | | | 330 | | | | | 335 | |
| Pro | Val | Asp | Pro | Ala | Phe | Trp | His | Gln | Gln | Tyr | Ser | Ala | Ala | Arg | Lys |
| | | | 340 | | | | | 345 | | | | | 350 | | |
| Trp | Gly | Pro | Gln | Ala | Ala | Ala | Val | Thr | Gln | Gly | Thr | Pro | Cys | Val | Pro |
| | | 355 | | | | | 360 | | | | | 365 | | | |
| Leu | Pro | Arg | Phe | Pro | Val | Pro | His | Pro | Ile | Tyr | Ser | Arg | Pro | Ala | Met |
| | 370 | | | | | 375 | | | | | 380 | | | | |
| Val | Pro | Pro | Pro | Pro | Ser | Thr | Thr | Lys | Leu | Ala | Gln | Leu | His | Leu | Glu |

```
                385                 390                 395                 400
Leu Gln Ala His Pro Ser Lys Glu Ser Ile Asp Ala Ala Ile Gly Asp
                405                 410                 415

Val Leu Val Lys Pro Trp Leu Pro Leu Pro Leu Gly Leu Lys Pro Pro
                420                 425                 430

Ser Leu Asp Ser Val Met Ser Glu Leu His Lys Gln Gly Val Pro Lys
                435                 440                 445

Ile Pro Pro Ala Ala Ala Thr Thr Thr Gly Ala Thr Gly
                450                 455                 460

<210> SEQ ID NO 7
<211> LENGTH: 681
<212> TYPE: DNA
<213> ORGANISM: Oryza sativa
<220> FEATURE:
<221> NAME/KEY: misc_feature
<223> OTHER INFORMATION: Partial sequence from the OsGLK1 gene

<400> SEQUENCE: 7
gcgaaggtgg actggacgcc tgagcttcac cggaggttcg tgcaggcggt ggagcagctc      60
ggcatcgaca aggccgtgcc gtcgaggata cttgagatca tggggatcga ctctctcacc     120
cggcacaaca tagccagcca tcttcagaag taccggtcac acagaaaaca catgattgcg     180
agagaggcgg aggcagcgag ttggacccaa cggcggcaga tttacgccgc cggtggaggt     240
gctgttgcga agaggccgga gtccaacgcg tggaccgtgc aaccattgg cttccctcct      300
cctccgccac caccaccatc accggctccg attcaacatt tgctcgcccc gttgcatgtt     360
tggggccacc cgacgatgga cccgtcccga gttccagtgt ggccaccgcg gcacctcgtt     420
ccccgtggcc cggcgccacc atgggttcca ccgccgccgc cgtcggaccc tgctttctgg     480
caccacccctt acatgagggg gccagcacat gtgccaactc aagggacacc ttgcatggcg     540
atgcccatgc cagctgcgag atttcctgct ccaccggtgc caggagttgt cccgtgtcca     600
atgtataggc cattgactcc accagcactg gcgagcaaga atcagcagga cgcacagctt     660
caactccagg ttcaaccatc a                                               681

<210> SEQ ID NO 8
<211> LENGTH: 227
<212> TYPE: PRT
<213> ORGANISM: Oryza sativa
<220> FEATURE:
<221> NAME/KEY: misc_feature
<223> OTHER INFORMATION: Partial protein sequence from the OsGLK1 gene

<400> SEQUENCE: 8

Ala Lys Val Asp Trp Thr Pro Glu Leu His Arg Arg Phe Val Gln Ala
1               5                  10                  15

Val Glu Gln Leu Gly Ile Asp Lys Ala Val Pro Ser Arg Ile Leu Glu
                20                  25                  30

Ile Met Gly Ile Asp Ser Leu Thr Arg His Asn Ile Ala Ser His Leu
            35                  40                  45

Gln Lys Tyr Arg Ser His Arg Lys His Met Ile Ala Arg Glu Ala Glu
        50                  55                  60

Ala Ala Ser Trp Thr Gln Arg Arg Gln Ile Tyr Ala Ala Gly Gly Gly
65                  70                  75                  80

Ala Val Ala Lys Arg Pro Glu Ser Asn Ala Trp Thr Val Pro Thr Ile
                85                  90                  95

Gly Phe Pro Pro Pro Pro Pro Pro Pro Ser Pro Ala Pro Ile Gln
```

```
            100                 105                 110
His Phe Ala Arg Pro Leu His Val Trp Gly His Pro Thr Met Asp Pro
        115                 120                 125

Ser Arg Val Pro Val Trp Pro Pro Arg His Leu Val Pro Arg Gly Pro
130                 135                 140

Ala Pro Pro Trp Val Pro Pro Pro Pro Ser Asp Pro Ala Phe Trp
145                 150                 155                 160

His His Pro Tyr Met Arg Gly Pro Ala His Val Pro Thr Gln Gly Thr
                165                 170                 175

Pro Cys Met Ala Met Pro Met Pro Ala Ala Arg Phe Pro Ala Pro Pro
        180                 185                 190

Val Pro Gly Val Val Pro Cys Pro Met Tyr Arg Pro Leu Thr Pro Pro
        195                 200                 205

Ala Leu Ala Ser Lys Asn Gln Gln Asp Ala Gln Leu Gln Leu Gln Val
    210                 215                 220

Gln Pro Ser
225

<210> SEQ ID NO 9
<211> LENGTH: 19
<212> TYPE: DNA
<213> ORGANISM: Artificial Sequence
<220> FEATURE:
<223> OTHER INFORMATION: G1 promoter_F

<400> SEQUENCE: 9
ccaaccctgc atatcttgc                                              19

<210> SEQ ID NO 10
<211> LENGTH: 20
<212> TYPE: DNA
<213> ORGANISM: Artificial Sequence
<220> FEATURE:
<223> OTHER INFORMATION: G1 promoter_R

<400> SEQUENCE: 10
ggcgacactg caagcatatc                                             20

<210> SEQ ID NO 11
<211> LENGTH: 20
<212> TYPE: DNA
<213> ORGANISM: Artificial sequence
<220> FEATURE:
<223> OTHER INFORMATION: G2 promoter_F

<400> SEQUENCE: 11
gctatctcca accacggctc                                             20

<210> SEQ ID NO 12
<211> LENGTH: 20
<212> TYPE: DNA
<213> ORGANISM: Artificial sequence
<220> FEATURE:
<223> OTHER INFORMATION: G2 promoter_R

<400> SEQUENCE: 12
cttgctgccg ctgctagtag                                             20

<210> SEQ ID NO 13
<211> LENGTH: 20
<212> TYPE: DNA
<213> ORGANISM: Artificial sequence
```

```
<220> FEATURE:
<223> OTHER INFORMATION: G1 cDNA_F

<400> SEQUENCE: 13
atgcttgcag tgtcgccgtc                                           20

<210> SEQ ID NO 14
<211> LENGTH: 21
<212> TYPE: DNA
<213> ORGANISM: Artificial sequence
<220> FEATURE:
<223> OTHER INFORMATION: G1 cDNA_R

<400> SEQUENCE: 14
tcatccacaa gcttgcggca c                                         21

<210> SEQ ID NO 15
<211> LENGTH: 24
<212> TYPE: DNA
<213> ORGANISM: Artificial sequence
<220> FEATURE:
<223> OTHER INFORMATION: G2 cDNA_F

<400> SEQUENCE: 15
atgcttgagg tgtcgacgct gcgc                                      24

<210> SEQ ID NO 16
<211> LENGTH: 20
<212> TYPE: DNA
<213> ORGANISM: Artificial sequence
<220> FEATURE:
<223> OTHER INFORMATION: G2 cDNA_R

<400> SEQUENCE: 16
tcatccggtg gcgccggtgg                                           20

<210> SEQ ID NO 17
<211> LENGTH: 27
<212> TYPE: DNA
<213> ORGANISM: Artificial sequence
<220> FEATURE:
<223> OTHER INFORMATION: G1p_F (XbaI)

<400> SEQUENCE: 17
cgtctagacc aaccgctgca tatcttg                                   27

<210> SEQ ID NO 18
<211> LENGTH: 26
<212> TYPE: DNA
<213> ORGANISM: Artificial sequence
<220> FEATURE:
<223> OTHER INFORMATION: G1p_R (BhI)

<400> SEQUENCE: 18
caggatccgg cgacactgca agcata                                    26

<210> SEQ ID NO 19
<211> LENGTH: 20
<212> TYPE: DNA
<213> ORGANISM: Artificial sequence
<220> FEATURE:
<223> OTHER INFORMATION: G2p_mF (HdIII)

<400> SEQUENCE: 19
tggcttggca catgaagctt                                           20
```

```
<210> SEQ ID NO 20
<211> LENGTH: 26
<212> TYPE: DNA
<213> ORGANISM: Artificial sequence
<220> FEATURE:
<223> OTHER INFORMATION: G2p_R (BhI)

<400> SEQUENCE: 20
caggatccac ttgctgccgc tgctag                                        26

<210> SEQ ID NO 21
<211> LENGTH: 23
<212> TYPE: DNA
<213> ORGANISM: Artificial sequence
<220> FEATURE:
<223> OTHER INFORMATION: G1_cDNA_F (BglII)

<400> SEQUENCE: 21
ggagatctat gcttgcagtg tcg                                           23

<210> SEQ ID NO 22
<211> LENGTH: 25
<212> TYPE: DNA
<213> ORGANISM: Artificial sequence
<220> FEATURE:
<223> OTHER INFORMATION: G1_cDNA_R (BglII)

<400> SEQUENCE: 22
ggagatcttc atccacaagc ttgcg                                         25

<210> SEQ ID NO 23
<211> LENGTH: 23
<212> TYPE: DNA
<213> ORGANISM: Artificial sequence
<220> FEATURE:
<223> OTHER INFORMATION: G2_cDNA_F (BglII)

<400> SEQUENCE: 23
ggagatctat gcttgaggtg tcg                                           23

<210> SEQ ID NO 24
<211> LENGTH: 23
<212> TYPE: DNA
<213> ORGANISM: Artificial sequence
<220> FEATURE:
<223> OTHER INFORMATION: G2_cDNA_F (BglII)

<400> SEQUENCE: 24
atagatcttc atccggtggc gcc                                           23

<210> SEQ ID NO 25
<211> LENGTH: 26
<212> TYPE: DNA
<213> ORGANISM: Artificial sequence
<220> FEATURE:
<223> OTHER INFORMATION: SP0

<400> SEQUENCE: 25
tcgagtttct ccataataat gtgtga                                        26

<210> SEQ ID NO 26
<211> LENGTH: 24
<212> TYPE: DNA
<213> ORGANISM: Artificial sequence
<220> FEATURE:
<223> OTHER INFORMATION: SP1
```

```
<400> SEQUENCE: 26
taatgtgtga gtagttccca gata                                              24

<210> SEQ ID NO 27
<211> LENGTH: 24
<212> TYPE: DNA
<213> ORGANISM: Artificial sequence
<220> FEATURE:
<223> OTHER INFORMATION: SP2

<400> SEQUENCE: 27
aatccagtac taaaatccag atcc                                              24

<210> SEQ ID NO 28
<211> LENGTH: 16
<212> TYPE: DNA
<213> ORGANISM: Artificial sequence
<220> FEATURE:
<223> OTHER INFORMATION: AD1
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 28
gtncgaswca nawgtt                                                       16

<210> SEQ ID NO 29
<211> LENGTH: 15
<212> TYPE: DNA
<213> ORGANISM: Artificial sequence
<220> FEATURE:
<223> OTHER INFORMATION: AD2
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 29
gwgnagwanc asaga                                                        15

<210> SEQ ID NO 30
<211> LENGTH: 15
<212> TYPE: DNA
<213> ORGANISM: Artificial sequence
<220> FEATURE:
<223> OTHER INFORMATION: AD3
<220> FEATURE:
<221> NAME/KEY: misc_feature
<222> LOCATION: (1)..(1)
<223> OTHER INFORMATION: n is a, c, g, or t

<400> SEQUENCE: 30
ntcgastwts gwgtt                                                        15

<210> SEQ ID NO 31
<211> LENGTH: 21
<212> TYPE: DNA
<213> ORGANISM: Artificial sequence
<220> FEATURE:
```

<223> OTHER INFORMATION: GT_F_G1

<400> SEQUENCE: 31
cgatcgtgtt ggcacgtgat g                                              21

<210> SEQ ID NO 32
<211> LENGTH: 23
<212> TYPE: DNA
<213> ORGANISM: Artificial sequence
<220> FEATURE:
<223> OTHER INFORMATION: GT_R_G1

<400> SEQUENCE: 32
tcgaagagtc aaccttcgag gtc                                            23

<210> SEQ ID NO 33
<211> LENGTH: 22
<212> TYPE: DNA
<213> ORGANISM: Artificial sequence
<220> FEATURE:
<223> OTHER INFORMATION: GT_F_G2

<400> SEQUENCE: 33
gccttggagg aagtagaaca gc                                             22

<210> SEQ ID NO 34
<211> LENGTH: 23
<212> TYPE: DNA
<213> ORGANISM: Artificial sequence
<220> FEATURE:
<223> OTHER INFORMATION: GT_R_G2

<400> SEQUENCE: 34
gtaggtttgg gaaatctttc agc                                            23

<210> SEQ ID NO 35
<211> LENGTH: 21
<212> TYPE: DNA
<213> ORGANISM: Artificial sequence
<220> FEATURE:
<223> OTHER INFORMATION: GT_F_G1G2

<400> SEQUENCE: 35
gtgaccggaa tccctctcaa g                                              21

<210> SEQ ID NO 36
<211> LENGTH: 21
<212> TYPE: DNA
<213> ORGANISM: Artificial sequence
<220> FEATURE:
<223> OTHER INFORMATION: GT_R_G1G2

<400> SEQUENCE: 36
gttgcactgt gtgtactagt c                                              21

<210> SEQ ID NO 37
<211> LENGTH: 19
<212> TYPE: DNA
<213> ORGANISM: Artificial sequence
<220> FEATURE:
<223> OTHER INFORMATION: G1p_F

<400> SEQUENCE: 37
ccaaccgctg catatcttg                                                 19

<210> SEQ ID NO 38
<211> LENGTH: 18
<212> TYPE: DNA
<213> ORGANISM: Artificial sequence
<220> FEATURE:
<223> OTHER INFORMATION: G1p_R

<400> SEQUENCE: 38
ggcgacactg caagcata                                                 18

<210> SEQ ID NO 39
<211> LENGTH: 20
<212> TYPE: DNA
<213> ORGANISM: Artificial sequence
<220> FEATURE:
<223> OTHER INFORMATION: G2p_F

<400> SEQUENCE: 39
tggcttggca catgaagctt                                               20

<210> SEQ ID NO 40
<211> LENGTH: 19
<212> TYPE: DNA
<213> ORGANISM: Artificial sequence
<220> FEATURE:
<223> OTHER INFORMATION: G2p_R

<400> SEQUENCE: 40
cacttgctgc cgctgctag                                                19

<210> SEQ ID NO 41
<211> LENGTH: 22
<212> TYPE: DNA
<213> ORGANISM: Artificial sequence
<220> FEATURE:
<223> OTHER INFORMATION: G1_mF

<400> SEQUENCE: 41
gtcgttctgg caccatgctt ac                                            22

<210> SEQ ID NO 42
<211> LENGTH: 21
<212> TYPE: DNA
<213> ORGANISM: Artificial sequence
<220> FEATURE:
<223> OTHER INFORMATION: G2_mF

<400> SEQUENCE: 42
cgcacagaaa gcacctgatg g                                             21

<210> SEQ ID NO 43
<211> LENGTH: 20
<212> TYPE: DNA
<213> ORGANISM: Artificial sequence
<220> FEATURE:
<223> OTHER INFORMATION: NOS_R

<400> SEQUENCE: 43
tcatcgcaag accggcaaca                                               20

<210> SEQ ID NO 44
<211> LENGTH: 21
<212> TYPE: DNA
<213> ORGANISM: Artificial sequence
<220> FEATURE:
<223> OTHER INFORMATION: G1-F1 qPCR

```
<400> SEQUENCE: 44
gcacataggc gccgtggatc c                                              21

<210> SEQ ID NO 45
<211> LENGTH: 21
<212> TYPE: DNA
<213> ORGANISM: Artificial sequence
<220> FEATURE:
<223> OTHER INFORMATION: G1-R1 qPCR

<400> SEQUENCE: 45
ttaccggcgg ctgctacctc g                                              21

<210> SEQ ID NO 46
<211> LENGTH: 26
<212> TYPE: DNA
<213> ORGANISM: Artificial sequence
<220> FEATURE:
<223> OTHER INFORMATION: G2-F qPCR

<400> SEQUENCE: 46
gacaaaggtg tagcagtagc cgccgc                                         26

<210> SEQ ID NO 47
<211> LENGTH: 26
<212> TYPE: DNA
<213> ORGANISM: Artificial sequence
<220> FEATURE:
<223> OTHER INFORMATION: G2-R qPCR

<400> SEQUENCE: 47
cgttggagtt cttgcccgcc gacttc                                         26

<210> SEQ ID NO 48
<211> LENGTH: 21
<212> TYPE: DNA
<213> ORGANISM: Artificial sequence
<220> FEATURE:
<223> OTHER INFORMATION: OsGLK1-F qPCR

<400> SEQUENCE: 48
gatgctggca tggaggtcgt c                                              21

<210> SEQ ID NO 49
<211> LENGTH: 21
<212> TYPE: DNA
<213> ORGANISM: Artificial sequence
<220> FEATURE:
<223> OTHER INFORMATION: OsGLK1-R qPCR

<400> SEQUENCE: 49
tgcacacctt cgcctccact c                                              21

<210> SEQ ID NO 50
<211> LENGTH: 21
<212> TYPE: DNA
<213> ORGANISM: Artificial sequence
<220> FEATURE:
<223> OTHER INFORMATION: OsGLK2-F qPCR

<400> SEQUENCE: 50
gtgacgacgg aggattcctc g                                              21

<210> SEQ ID NO 51
<211> LENGTH: 21
```

<212> TYPE: DNA
<213> ORGANISM: Artificial sequence
<220> FEATURE:
<223> OTHER INFORMATION: OsGLK2-R qPCR

<400> SEQUENCE: 51
ccgatgacga cgacgacgac g                                           21

<210> SEQ ID NO 52
<211> LENGTH: 23
<212> TYPE: DNA
<213> ORGANISM: Artificial sequence
<220> FEATURE:
<223> OTHER INFORMATION: OsFRD3_F_exon 1

<400> SEQUENCE: 52
cgcgctgtcc aaggcctatc tct                                         23

<210> SEQ ID NO 53
<211> LENGTH: 22
<212> TYPE: DNA
<213> ORGANISM: Artificial sequence
<220> FEATURE:
<223> OTHER INFORMATION: OsFRD3_R_exon 1

<400> SEQUENCE: 53
gcaacagcat ggggagcatt gg                                          22

<210> SEQ ID NO 54
<211> LENGTH: 22
<212> TYPE: DNA
<213> ORGANISM: Artificial sequence
<220> FEATURE:
<223> OTHER INFORMATION: OsFRD3_F_exon 6

<400> SEQUENCE: 54
ggcttggcat aactggagct gc                                          22

<210> SEQ ID NO 55
<211> LENGTH: 22
<212> TYPE: DNA
<213> ORGANISM: Artificial sequence
<220> FEATURE:
<223> OTHER INFORMATION: OsFRD3_R_exon 6-7

<400> SEQUENCE: 55
aactcaaagc ccctgggag ag                                           22

<210> SEQ ID NO 56
<211> LENGTH: 25
<212> TYPE: DNA
<213> ORGANISM: Artificial sequence
<220> FEATURE:
<223> OTHER INFORMATION: OsFRD3_F_exon 7

<400> SEQUENCE: 56
ggtggcatgc tgttaggaag aaccc                                       25

<210> SEQ ID NO 57
<211> LENGTH: 23
<212> TYPE: DNA
<213> ORGANISM: Artificial sequence
<220> FEATURE:
<223> OTHER INFORMATION: OsFRD3_R_exon 7

<400> SEQUENCE: 57

```
gccatagctg ttgggccttg tcg                                              23

<210> SEQ ID NO 58
<211> LENGTH: 22
<212> TYPE: DNA
<213> ORGANISM: Artificial sequence
<220> FEATURE:
<223> OTHER INFORMATION: 17S rRNA_F

<400> SEQUENCE: 58
gataactcga cggatcgcac gg                                               22

<210> SEQ ID NO 59
<211> LENGTH: 23
<212> TYPE: DNA
<213> ORGANISM: Artificial sequence
<220> FEATURE:
<223> OTHER INFORMATION: 17S rRNA_R

<400> SEQUENCE: 59
gcctgctgcc ttccttggat gtg                                              23

<210> SEQ ID NO 60
<211> LENGTH: 22
<212> TYPE: DNA
<213> ORGANISM: Artificial sequence
<220> FEATURE:
<223> OTHER INFORMATION: OsActin_F

<400> SEQUENCE: 60
atccttgtat gctagcggtc ga                                               22

<210> SEQ ID NO 61
<211> LENGTH: 21
<212> TYPE: DNA
<213> ORGANISM: Artificial sequence
<220> FEATURE:
<223> OTHER INFORMATION: OsActin_R

<400> SEQUENCE: 61
atccaaccgg aggatagcat g                                                21

<210> SEQ ID NO 62
<211> LENGTH: 21
<212> TYPE: DNA
<213> ORGANISM: Artificial sequence
<220> FEATURE:
<223> OTHER INFORMATION: HptII_F

<400> SEQUENCE: 62
gacctgatgc agctctcgga g                                                21

<210> SEQ ID NO 63
<211> LENGTH: 22
<212> TYPE: DNA
<213> ORGANISM: Artificial sequence
<220> FEATURE:
<223> OTHER INFORMATION: HptII_R

<400> SEQUENCE: 63
tgctccatac aagccaacca cg                                               22
```

APPROACHES TO DRAMATICALLY INCREASE RICE PRODUCTIVITY

CROSS-REFERENCE TO RELATED APPLICATIONS

This application is the National Stage of International Application No. PCT/US2021/029863, filed on Apr. 29, 2021, which claims priority to U.S. Provisional Application No. 63/019,672, filed on May 4, 2020. The contents of both applications are hereby incorporated by reference in their entirety.

SEQUENCE LISTING

A computer readable file containing a sequence listing is being electronically co-filed herewith via EFS-Web. The computer readable file, submitted under 37 CFR § 1.821 (e), will also serve as the copy required by 37 § CFR 1.821 (c). The file (filename "40K6236.TXT") was created on Nov. 1, 2022 and has a size of 41,541 bytes.

The content of the computer readable file is hereby incorporated by reference in its entirety.

BACKGROUND

Expanding human populations demand increased crop production. To meet this demand, recent efforts have focused on increasing photosynthetic efficiency of crops such as rice. A set of initiatives from the early 1960s to the year 2000 for increasing worldwide agricultural production, i.e., the so-called Green Revolution, resulted in approximately a doubling in rice yield. However, improvements in yield have been less impressive in recent years.

As more than 90% of crop biomass is generated from photosynthesis, increasing photosynthesis in major crops such as rice may significantly increase yield.

Chloroplasts play an essential role in photosynthesis and also are the sites for biosynthesis of phytohormones that regulate plant growth, development, and stress tolerance. A pair of Golden 2-like (GLK) transcription factor genes is known to regulate chloroplast development in higher plants such as maize (a $C_4$ plant) and rice (a $C_3$ plant). Through evolution, the GLK genes from maize, in particular GLK2, may have acquired new and stronger functions, as compared to rice GLK genes.

As photosynthesis is more efficient in maize than in rice, transforming the two maize GLK genes into the rice genome may enhance the photosynthesis of the transgenic rice plants, leading to increased rice yield.

It has recently been reported that transforming either of the two maize GLK genes, particularly the maize GLK2 gene, controlled by the maize ubiquitin promoter increased rice yield by 16-40%. However, the use of the maize ubiquitin promoter, a strong constitutive promoter, to drive the expression of the maize GLK genes in transgenic rice resulted in smaller seeds.

There is still a strong need to increase rice yield to meet the demands of human population growth.

SUMMARY

To meet the increasing food demands of growing human populations, a transgenic rice plant is provided that includes in its genome a recombinant DNA construct that contains a first nucleic acid having a sequence of a first Golden 2-like transcription factor (GLK) gene operably linked to its natural promoter and 5' untranslated region (5'UTR), and a second nucleic acid having a sequence of a second GLK gene operably linked to its natural promoter and 5'UTR, the second GLK gene being distinct from the first GLK gene. The first GLK gene and the second GLK gene are both heterologous, i.e., not from rice, and the transgenic rice plant exhibits a dramatic, i.e., at least 50%, increase in shoot biomass (65-106%) and grain yield (50-95%), as compared to an untransformed wild-type rice plant.

A method for producing the transgenic rice plant described above is also provided.

Further disclosed is a recombinant DNA construct that can be used in the method. The recombinant DNA construct includes a first nucleic acid sequence that includes a first GLK gene operably linked to its natural promoter and 5'UTR, and a second nucleic acid sequence that includes a second GLK gene operably linked to its natural promoter and 5'UTR, the second GLK gene being distinct from the first GLK gene. The first GLK gene and the second GLK gene are from a $C_4$ plant, e.g., maize.

The details of several embodiments of the present invention are set forth in both the description and the drawings below. All features, objects, and advantages of the invention will be apparent from the description and the drawings, as well as from the appended claims.

BRIEF DESCRIPTION OF THE DRAWINGS

The description below refers to the accompanying drawings, of which:

FIG. 6B shows GO term enrichment analysis of differentially expressed genes in young shoot of transgenic plants (labeled as above) relative to WT. Filled boxes indicate up-regulated (left panel) or down-regulated (right panel) biological processes.

DETAILED DESCRIPTION

Figure 1:
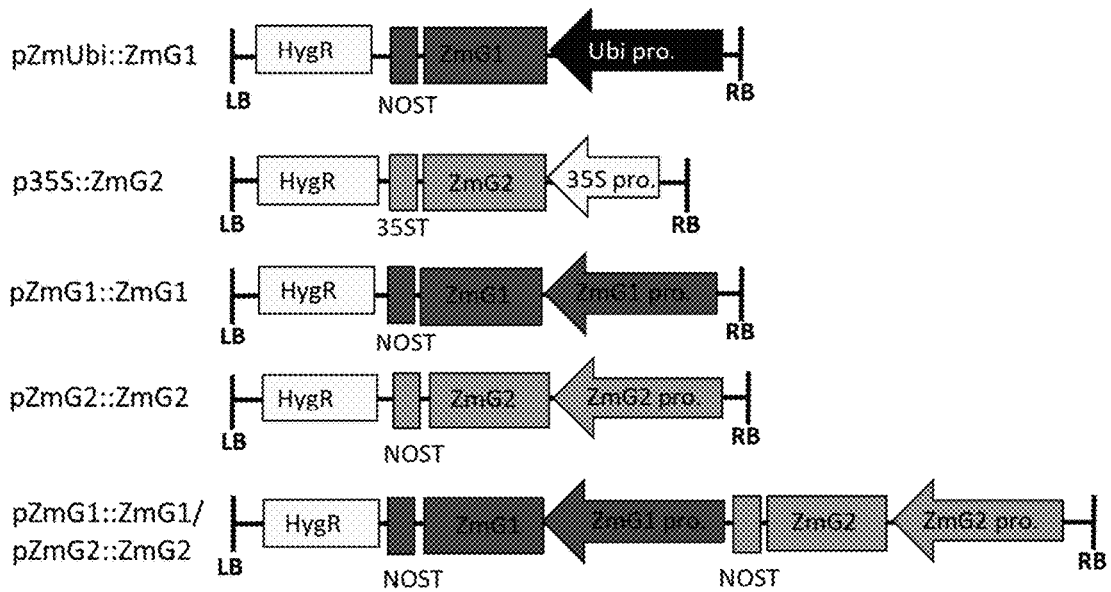
FIG. 1 is a diagram of five maize GLK constructs used for *Agrobacterium*-mediated rice transformation to compare their effects on gene expression and plant growth and yield. pUbi: ubiquitin promoter; p35S: 35S promoter; Zm *Zea mays* (maize); pZmG1::ZmG1: maize GLK1 construct with its own promoter and 5'UTR; pZmG2::ZmG2: maize GLK2 construct with its own promoter and 5'UTR; HygR: hygromycin resistant gene; ZmG1: maize GLK1 gene; ZmG2 maize GLK2 gene; 35ST: 35S terminator; NOST: nopaline synthase (nos) terminator; pro: promoter; LB: left border; and RB: right border.
Figure 2A:
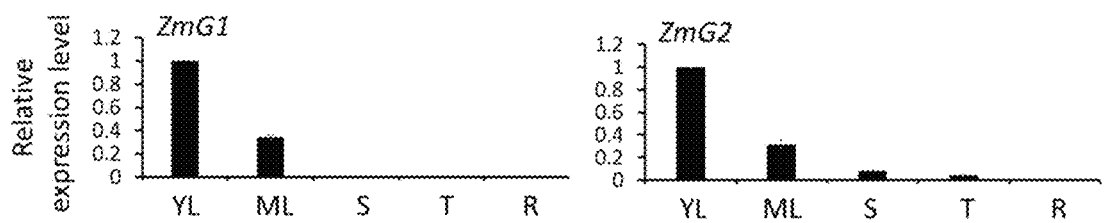
FIG. 2A shows plots of relative gene expression levels of ZmG1 (left) and ZmG2 (right) in different maize tissues determined by quantitative real-time polymerase chain reaction ("qRT-PCR") of total RNA isolated from young leaf (YL) of 9-day old seedlings, mature leaves (ML) of 2-month-old plants, and young stems (S), tassels (T), and roots (R). Values are means±S.D. of three replicates and are normalized to the expression level of 17S rRNA.
Figure 2B:
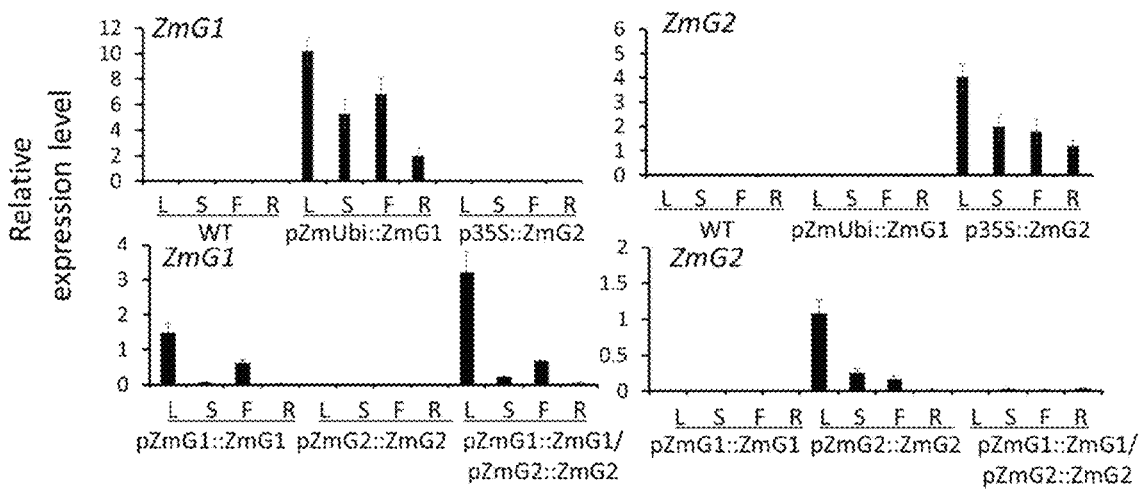
FIG. 2B shows plots of relative gene expression levels of ZmG1 (left) and ZmG2 (right) determined by qRT-PCR in total RNA from wild-type (WT) and transgenic rice plants. Transgenic rice plants carry the transgene constructs labeled as in FIG. 1. Total RNA was isolated from mature leaves (L), stems (S), florets (F), and roots (R). Heterozygous pZmG2::ZmG2 plants and the homozygous plants of other four transgenic plants are shown; the homozygous pZmG2::ZmG2 plants died after two months of cultivation due to high gene expression levels. Values are means±S.D. of three replicates and are normalized to the expression level of 17S rRNA.
Figure 2C:
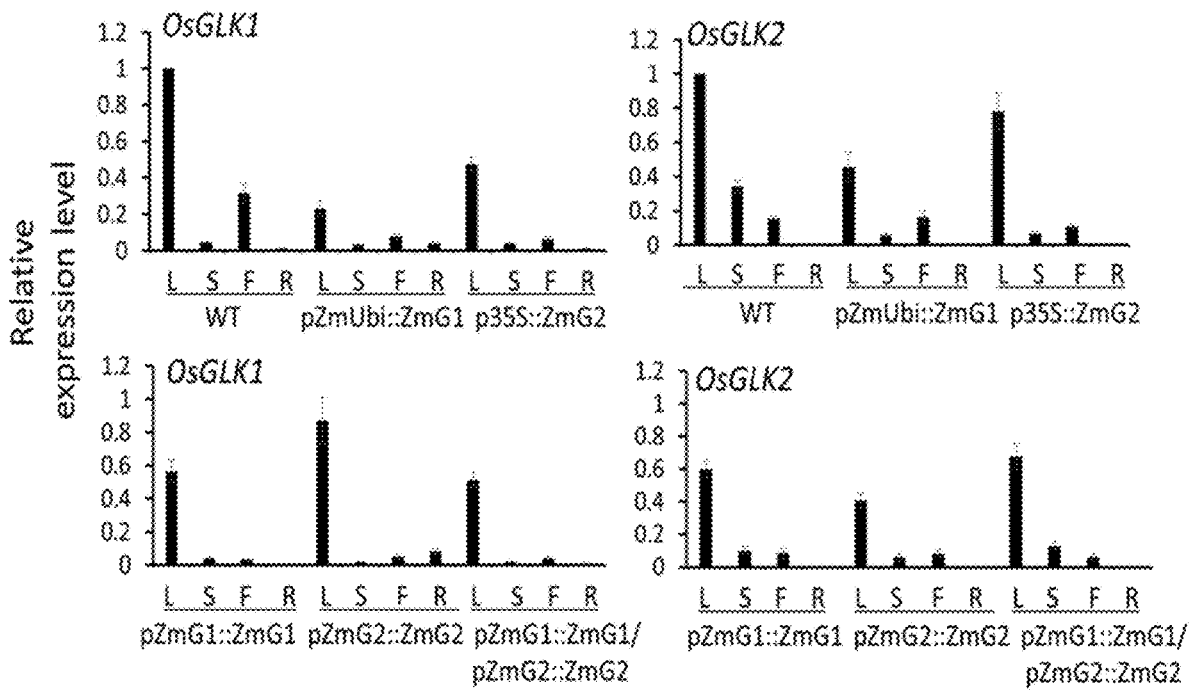
FIG. 2C includes plots of expression levels of OsGLK1 and OsGLK2 in different tissues of WT and transgenic rice plants measured by qRT-PCR. Tissue sources and transgenic rice plants are as described in the legend to FIG. 2B. Values are means±S.D. of three replicates and are normalized to the expression level of 17S rRNA.
Figure 2D:
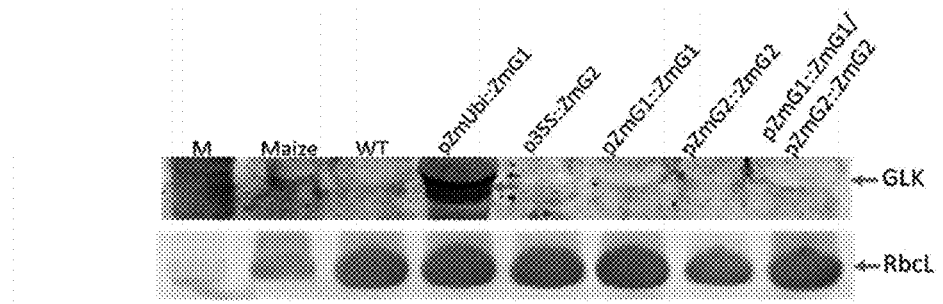
FIG. 2D shows Western blot analysis of GLK proteins in young maize leaves, mature WT rice flag leaves, and transgenic rice flag leaves using antibodies raised against the consensus peptide of both rice and maize GLK proteins. The same amount of total leaf protein (20 μg) was loaded in each lane. RbcL serves as an internal control and maize leaf protein was included as a positive control for GLK. M: molecular weight markers.

As summarized above, a transgenic rice plant is provided that contains in its genome two distinct and heterologous GLK genes, each of which is under the control of its natural promoter and 5'UTR. For example, both GLK genes can be from a $C_4$ plant. Exemplary $C_4$ plant sources for the GLK genes include, but are not limited to, *Zea mays* L. (maize), *Sorghum bicolor* L. (*Sorghum*), *Saccharum officinarum* L. (sugarcane), and *Setaria italica* L. (foxtail millet).

In a specific example, the first GLK gene is *Zea mays* GLK1 and the second GLK gene is *Zea mays* GLK2, also known as G2. More specifically, the protein expressed from the GLK1 gene has the amino acid sequence of SEQ ID NO: 3 and the protein expressed from the GLK2 gene has the amino acid sequence of SEQ ID NO: 6.

Moreover, the natural promoter and 5'UTR of the first GLK gene can have the sequence of SEQ ID NO: 1 and the natural promoter and 5'UTR of the second GLK gene can have the sequence of SEQ ID NO: 4.

As mentioned above, the transgenic rice plant exhibits a dramatic increase, i.e., at least 50%, in shoot growth and grain yield, as compared to an untransformed wild-type rice plant.

In a particular example, the increase in shoot growth in pZmG1::ZmG1/pZmG2::ZmG2 transgenic plants, as measured by biomass change, can range between 65% to 106%, as compared to an untransformed wild-type rice plant, e.g., rice cultivar Tainung 67 (TNG67).

In the same example, the grain yield in pZmG1::ZmG1/pZmG2::ZmG2 transgenic plants can be 50% to 95% higher than the untransformed wild-type rice plant.

Also mentioned in the SUMMARY section is a method for producing the transgenic plant described above. The method is carried out by (i) introducing into a host rice plant a recombinant DNA construct that contains a first GLK gene operably linked to its natural promoter and 5'UTR and a second GLK gene operably linked to its natural promoter and 5'UTR, and (ii) identifying a transgenic rice plant that exhibits at least a 50% increase in shoot biomass and grain yield, as compared to an untransformed wild-type rice plant, such as TNG67.

In this method, the first GLK gene and the second GLK gene are distinct from each other and heterologous to rice. In one example, the first GLK gene and the second GLK gene are from a C4 plant, e.g., maize, *Sorghum*, sugarcane, and foxtail millet. In a specific method, the first GLK gene is *Zea mays* GLK1 and the second GLK gene is *Zea mays* GLK2.

The recombinant DNA construct, in one example, can express a protein having the amino acid sequence of SEQ ID NO: 3, i.e., *Zea mays* GLK1, and a protein having the amino acid sequence of SEQ ID NO: 6, i.e., *Zea mays* GLK2.

The expression of GLK1 and GLK2 can be under the control of the natural promoter and 5'UTR having the sequence of SEQ ID NO: 1 and the natural promoter and 5'UTR having the sequence of SEQ ID NO: 4, respectively.

The grain yield of the identified transgenic rice plant is dramatically higher, as compared to the untransformed wild-type rice plant, e.g., TNG67. For example, a 50% to 95% increase in grain yield in a pZmG1::ZmG1/pZmG2::ZmG2 transgenic rice plant can be seen, as compared to the untransformed wild-type rice plant.

The shoot biomass of the transgenic rice plant is also dramatically higher than the untransformed wild-type rice plant. An exemplary pZmG1::ZmG1/pZmG2::ZmG2 transgenic rice plant has a shoot mass 65% to 106% higher than that of the untransformed wild-type rice plant.

Next discussed is the recombinant DNA construct mentioned in the SUMMARY section above. The recombinant DNA construct includes a first GLK gene operably linked to its natural promoter and 5'UTR, and a second GLK gene operably linked to its natural promoter and 5'UTR. The second GLK gene is distinct from the first GLK gene, and the two GLK genes are from a C4 plant. As such, they are heterologous to rice.

In an exemplary recombinant DNA construct, the first GLK gene is *Zea mays* GLK1 and the second GLK gene is *Zea mays* GLK2.

A particular recombinant DNA construct includes (i) a first GLK gene encoding the amino acid sequence of SEQ ID NO: 3 and being under the control of its natural promoter/5'UTR having the sequence of SEQ ID NO: 1 and (ii) a second GLK gene encoding the amino acid sequence of SEQ ID NO: 6 and being under the control of its natural promoter/5'UTR having the sequence of SEQ ID NO: 4.

In a specific recombinant DNA construct, the first GLK gene is encoded by a nucleic acid having the sequence of SEQ ID NO: 2 and the second GLK gene is encoded by a nucleic acid having the sequence of SEQ ID NO: 5.

Without further elaboration, it is believed that one skilled in the art can, based on the disclosure herein, utilize the present disclosure to its fullest extent. The following specific examples are, therefore, to be construed as merely descriptive, and not limitative of the remainder of the disclosure in any way whatsoever. All publications and patent documents cited herein are incorporated by reference in their entirety.

Example 1: Maize GLK Constructs Used for *Agrobacterium*-Mediated Rice Transformation Five maize GLK constructs were prepared by the standard techniques mentioned in Example 7 below and included the genes and regulatory sequences shown in FIG. 1.

Rice (*Oryza sativa* cv. TNG67) callus induction, co-cultivation with *Agrobacterium*, hygromycin selection of transformed callus, and plantlet regeneration were performed according to Yeh et al. 2015 (Rice 8:36-48). All positive transgenic seedlings were transplanted into soil and cultivated in a greenhouse for molecular, physiological, and anatomical analyses. Determination of transgene insertion location was done by thermal asymmetric interlaced (TAIL)-PCR. The conditions for TAIL-PCR were previously described in Liu et al. 2005 (Methods Mol. Biol. 286:341-348) and Møller et al. 2009 (Plant Cell 21:2163-2178). Screening for homozygous transgenic plants was performed by genotyping PCR using genotyping primers designed from the 3' and 5' end regions flanking the transgene insertion site as determined by Tail-PCR.

Example 2: Expression of Maize GLK Constructs in Transgenic Rice Plants

Expression levels of maize GLK genes were determined by qRT-PCR and by Western blot analysis as set forth in Example 7, infra. The results are shown in FIGS. 2A-2D.

The ubiquitin and 35S promoters over-drove the expression of maize GLK genes in all transgenic rice tissues studied. A large amount of GLK protein was detected in the leaves of pZmUbiZmG1 transgenic plants, reflecting the high expression level of ZmG1 in leaves. See FIG. 2B.

The heterozygous pZmG2::ZmG2 plants showed delayed growth and development by one month while the homozygous plants of pZmG2::ZmG2 seedlings died after two months of cultivation. This suggests that the high-level expression of maize GLK2 in pZmG2::ZmG2 plants inhibits plant growth and development.

The expression of ZmG1 was promoted whereas the expression of ZmG2 was suppressed in all studied tissues of pZmG1::ZmG1/pZmG2::ZmG2 transgenic plants, thereby providing evidence of coordinated expression of these two genes in pZmG1::ZmG1/pZmG2::ZmG2 transgenic rice.

The expression levels of rice endogenous GLK1 and GLK2 genes in maize GLK transgenic rice plants were generally reduced.

Figure 3A:
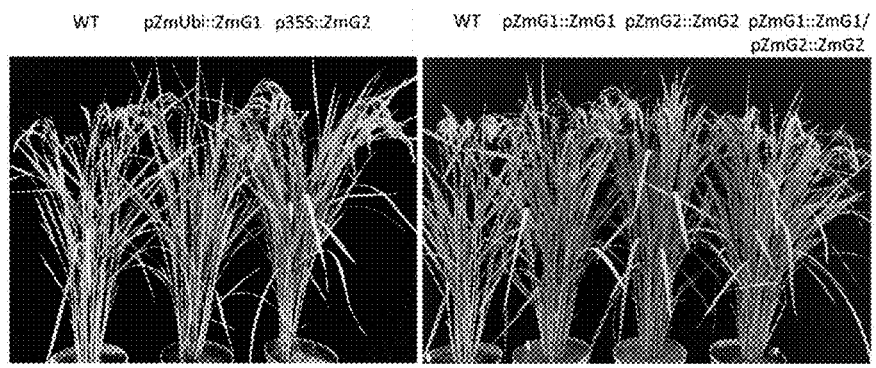
FIG. 3A shows photographs of 4-month old WT and transgenic rice plants. The transgenes are labeled as in FIG. 1 above.

Example 3: Characterization of Growth and Chloroplasts in Transgenic Rice Plants The flowering and seed setting of pZmG2::ZmG2 (heterozygous) rice plants were delayed by one month, as compared to all other tested rice plants. See FIG. 3A.

Transmission electron microscopy (TEM) analysis demonstrated that the expression of maize GLK genes in rice induced the development of large chloroplasts in both mesophyll (M) and bundle sheath (BS) cells in all five transgenic rice lines. Similar to WT, the M and BS chloroplast structures in all GLK transgenic rice plants had intact grana structures and thylakoid membranes.

Figure 3B:
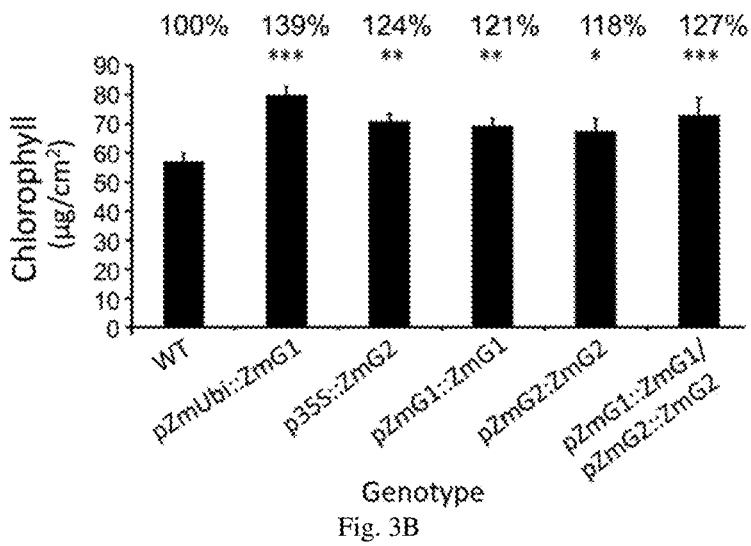
FIG. 3B is a bar graph of chlorophyll content per leaf area in the flag leaves of the indicated wild-type and transgenic rice plants, expressed as $\mu g/cm^2$. Shown above the graph is the relative chlorophyll content per leaf area expressed as percent relative to wild-type plants, set to 100%. Statistical significance versus WT is shown (*P<0.05;  P<0.01; *P<0.001). Data=mean±S.D., n=4 (each sample obtained from leaf sections of three different plants).
Figure 3C:
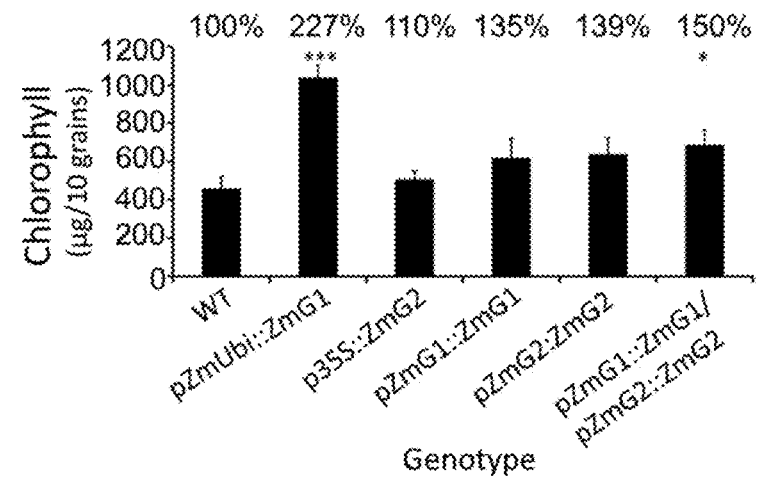
FIG. 3C is a bar graph of chlorophyll content per 10 grains in the florets of the indicated wild-type and transgenic rice plants, expressed as μg/10 grains. Constructs and statistical significance values are as set forth in the legend to FIG. 3B.
Figure 3D:
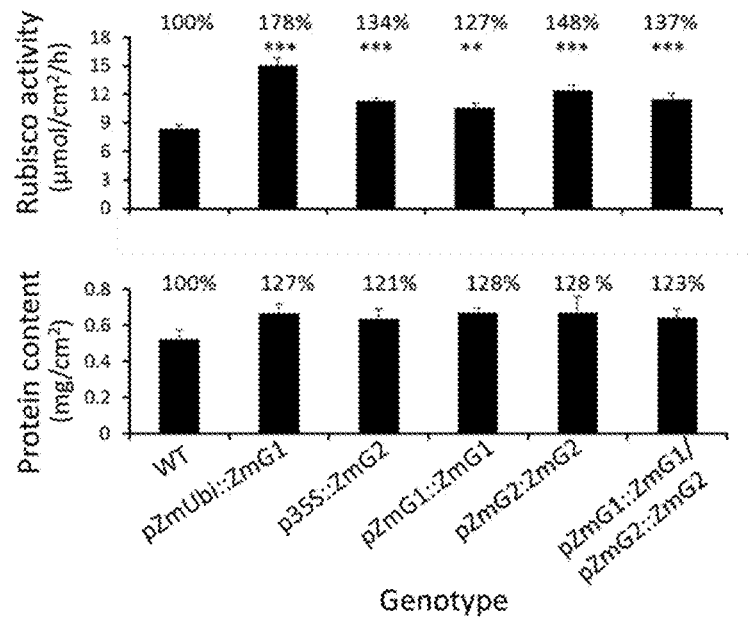
FIG. 3D shows bar graphs of Rubisco content analyzed by enzymatic activity (top panel) and total soluble protein content per leaf area in the flag leaves (lower panel). The statistical tests were based on the pairwise t-test. Asterisks indicate statistical significance levels in comparison with WT (*P<0.05;  P<0.01; *P<0.001). Data=means±S.D., n=4 (each sample was obtained from leaf sections of three different plants). Transgenic plants are as identified above.

Relative to WT, chlorophyll contents in the flag leaves and florets of all five GLK transgenic plants increased by 18-39% and 10-127%, respectively, and Rubisco activity and protein content increased in the flag leaves by 27-28% and 21-28%, respectively. See FIGS. 3B, 3C, and 3D. These observations were consistent with increased chloroplast development and expression of related genes.

Clearly, all photosynthetic functions in the five transgenic rice lines were significantly enhanced, particularly in the pZmG1::ZmG1/pZmG2::ZmG2 transgenic plants.

Example 4: Light-Saturated Photosynthetic Rates

Figure 4:
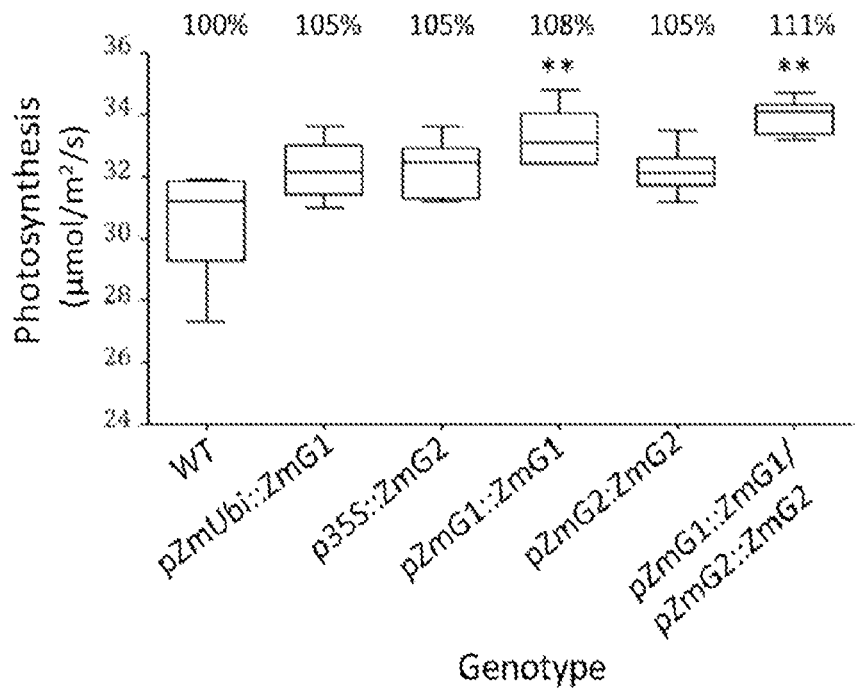
FIG. 4 shows light-saturated photosynthetic rates per leaf area in the flag leaves of 4-month old WT and GLK transgenic rice plants expressed as $\mu mol/m^2/s$. The plot shows value range, 25% to 75% quartiles (box), and mean (horizontal line). Measurement conditions were 2000 $\mu mol/m^2/s$ PPFD, 30° C., and 400 μL/L $CO_2$. The statistical tests were based on the Wilcoxon-Mann-Whitney U-test for non-parametric comparison of two groups. Asterisks indicate statistical significance in comparison with WT (**P<0.01, n=6). The constructs are as described above.

Flag leaves were analyzed for photosynthesis measurements, as they contribute more significantly to grain filling than other leaves. The flag leaf photosynthetic rates of all five GLK transgenic plants increased by 5-11% compared to WT. See FIG. 4. The highest photosynthetic rate was observed in the pZmG1::ZmG1/pZmG2::ZmG2 transgenic rice plants.

Example 5: Growth Traits and Grain Yields

Figure 5A:
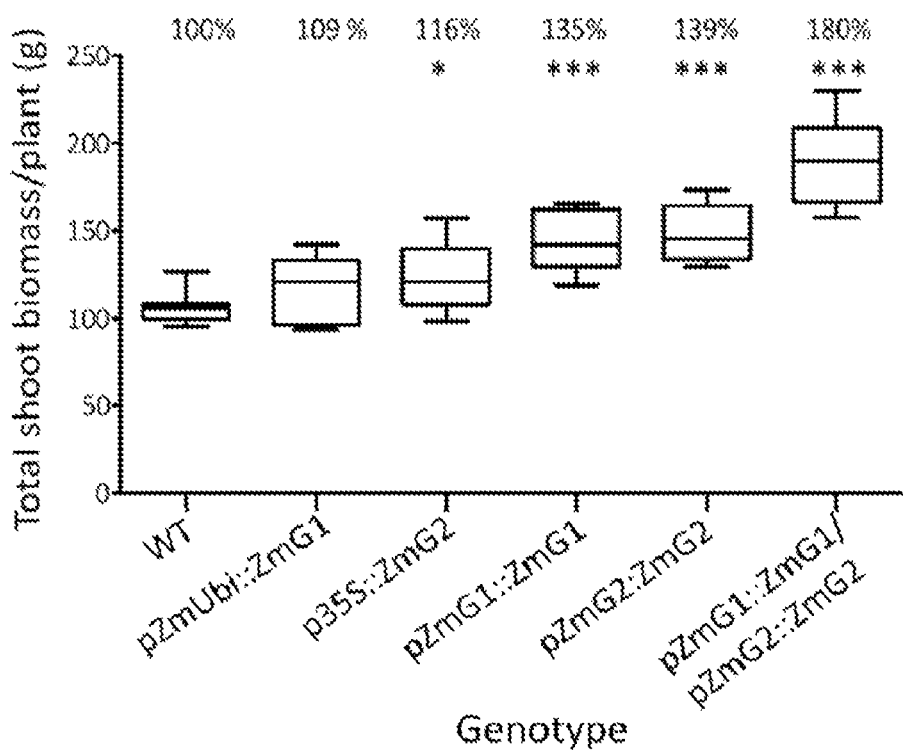
FIG. 5A shows total aboveground biomass dry weight/plant of WT and five GLK transgenic rice plants. Plants were grown in a greenhouse between May and September. Statistical test was as described above for FIG. 4. Asterisks indicate statistical significance levels (*P<0.05;  P<0.01; *P<0.001, n=9). The transgenic constructs are as shown in FIG. 1.
Figure 5B:
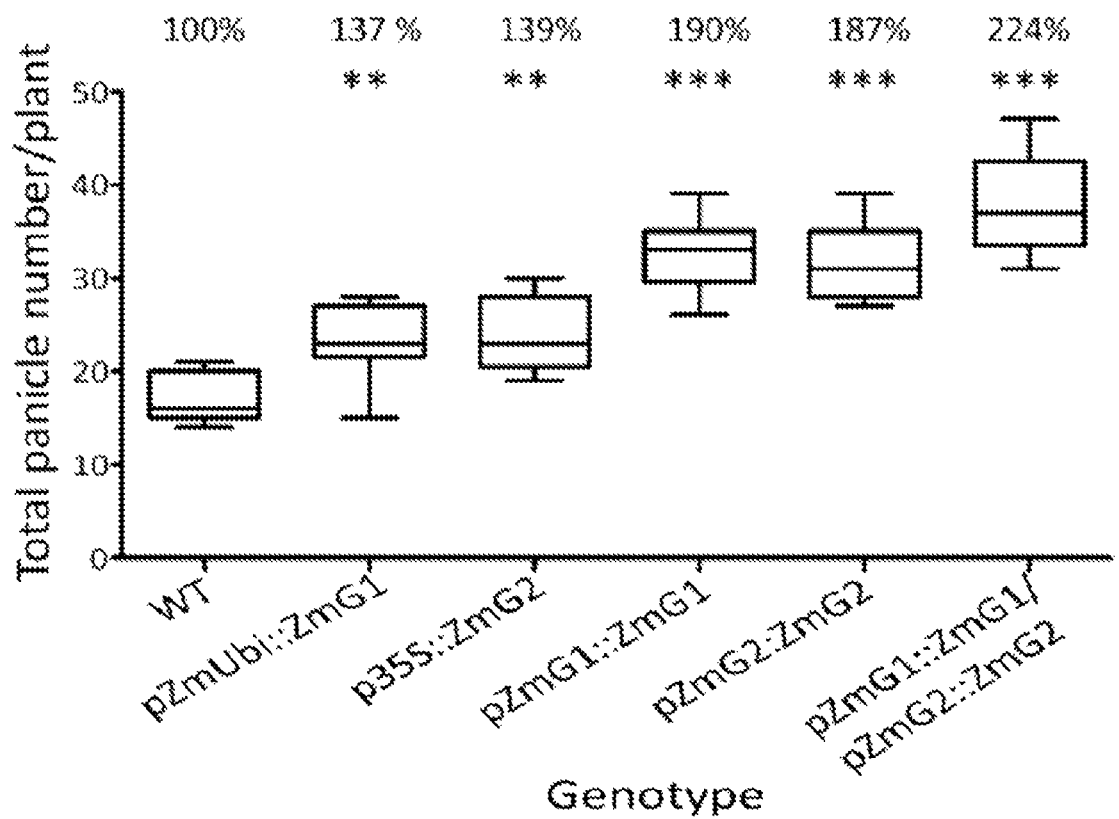
FIG. 5B is a plot of total panicle number per plant of WT and five GLK transgenic rice plants. Constructs and statistical analysis are as shown in the legend to FIG. 5A.

Compared to WT (100%), the total shoot biomass (109-180%) and total panicle number (137-224%) per plant increased in all five GLK transgenic plants, mainly due to production of extra tillers. See FIGS. 5A and 5B.

Figure 5C:
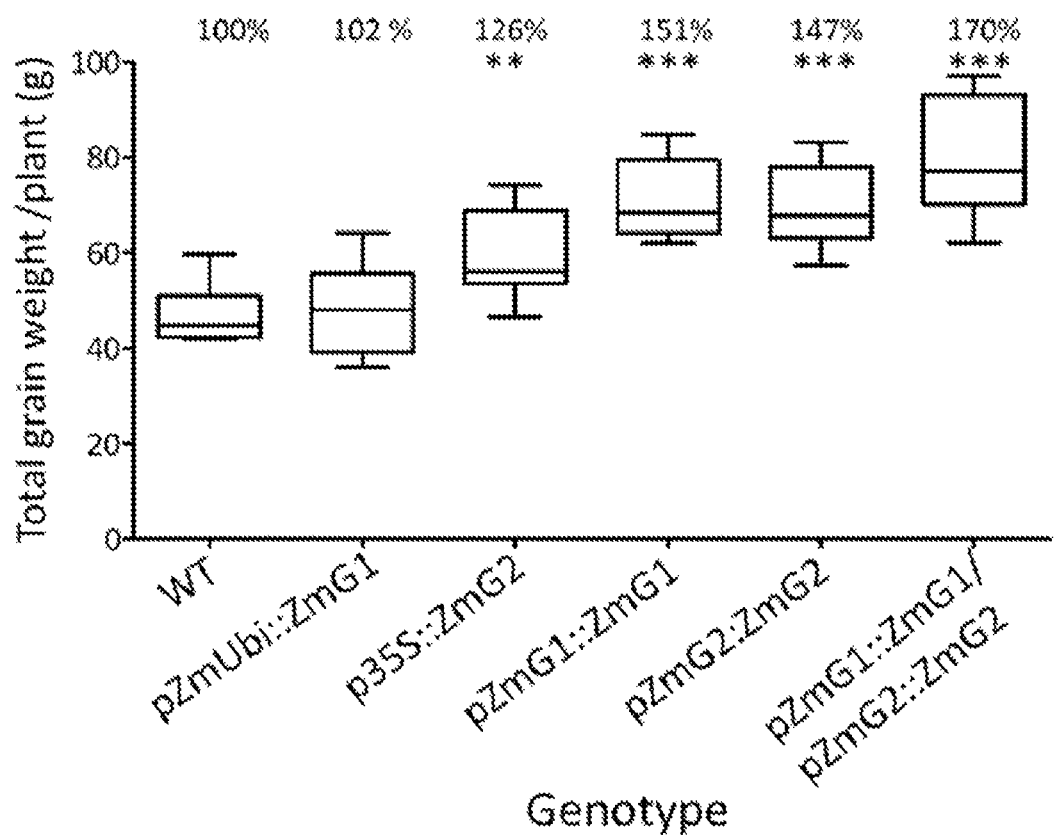
FIG. 5C shows total grain weight per plant of WT and the five GLK transgenic rice plants mentioned above. Constructs and statistical analysis are as shown in the legend to FIG. 5A.

Transgenic pZmG1::ZmG1 and pZmG2::ZmG2 (heterozygous) rice plants showed an increase in total grain weights per plant of 51% and 47%, respectively, which was accompanied by a modest decrease, i.e., 1-10%, in 1000-grain weight. See FIGS. 5C and 5D.

Surprisingly, pZmG1ZmG1/pZmG2::ZmG2 rice plants showed an increase of as high as 95% in total grain weight per plant, with an average increase of 70%. See FIG. 5C.

pZmUbi::ZmG1 plants showed no significant increase in total grain yield as a result of a 15% reduction in grain weight. Thus, although the constitutive ubiquitin promoter increased biomass (see FIG. 5A), it caused a reduction in reproductive growth.

Not to be bound by theory, it is thought that high level expression of maize GLK1, as driven by the strong maize ubiquitin promoter, may inhibit reproductive growth and development.

Example 6: Transcriptome Analysis of Transgenic Rice Plants

Total RNA was isolated from the shoots and roots of 4-day old seedlings of WT, pZmG1::ZmG1, pZmG2::ZmG2 and pZmG1::ZmG1/pZmG2::ZmG2 transgenic plants as previously described. See Liu et al. 2013 (PNAS 110:3979-3984). Transcriptome analysis was performed also as described in Liu et al. (2013). The results are shown in FIGS. 6A and 6B.

Figures 5D, 6A:
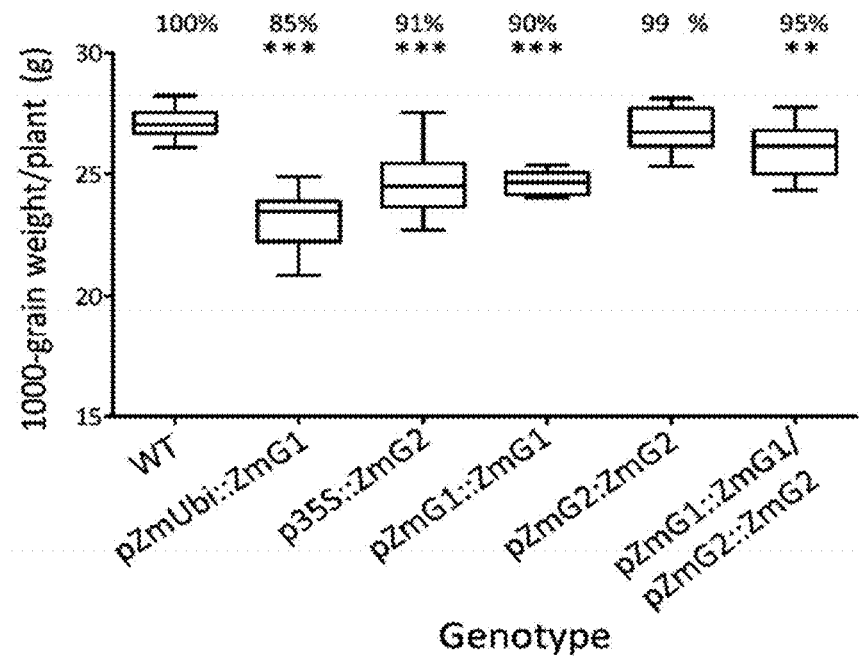
FIG. 5D shows the 1000-grain dry weight per plant of WT and the five GLK transgenic rice plants. Constructs and statistical analysis are as shown in the legend to FIG. 5A.
FIG. 6A shows the results of Gene Ontology (GO) term enrichment analysis with biological process category of differentially expressed genes in young shoots of pZmG1::ZmG1, pZmG2::ZmG2, and pZmG1::ZmG1/pZmG2::ZmG2 transgenic plants, relative to WT. Filled boxes indicate up-regulated (left panel) or down-regulated (right panel) biological processes.

Up-Regulated Differentially Expressed Genes pZmG2::ZmG2 shoots were significantly enriched in Gene Ontology (GO) terms related to responses to biotic/abiotic stimuli and chitin catabolic process (see FIG. 6A), whereas pZmG1::ZmG1/pZmG2::ZmG2 shoots were mainly enriched in lipid transport GO terms (FIG. 6B).

pZmG1::ZmG1 roots were significantly enriched in the regulation of transcription related GO terms, whereas pZmG2::ZmG2 roots were enriched in biotic stress response GO terms, including oxylipin biosynthetic process (methyl jasmonate biosynthesis pathway), chitin catabolic process, and phytoalexin metabolic process. Clearly, in rice, both maize GLK genes stimulate chloroplast development, but ZmG1 acts more as a transcriptional regulator and ZmG2 acts more as a defense regulator.

pZmG1::ZmG1/pZmG2::ZmG2 roots were enriched in the regulation of transcription related GO terms (also found in pZmG1::ZmG1 roots), chitin catabolic/phytoalexin biosynthetic processes (also found in pZmG2ZmG2 roots) and activation of photosynthesis related pathways, gibberellin (GA) metabolic processes, isoprenoid biosynthetic processes, xylan catabolic processes, and protein ubiquitylation.

Taken together, these results suggest that the two maize GLK genes promote rice photosynthesis, metabolism, and stress responses in a complementary manner Down-Regulated Differentially Expressed Genes pZmG2::ZmG2 roots showed enriched down-regulation of genes involved in ion transport, amine biosynthetic processes, sulfur compound biosynthetic processes, and aspartate family amino acid biosynthetic processes, whereas pZmG1::ZmG1/pZmG2::ZmG2 roots were mainly enriched in down-regulation of amine biosynthesis and ion transport. See FIGS. 6A and 6B. This implies that ZmG1 may partially offset the repressive functions of ZmG2 when they are co-expressed in rice. This is consistent with the observations that the seedlings of pZmG2::ZmG2 plants exhibited stunted growth in both shoot and root after germination, and that the homozygous pZmG2::ZmG2 plants with much higher expression of the ZmG2 gene died after two months of growth.

Example 7: Materials and Methods

Promoter and Gene Cloning

Genomic DNA was extracted from maize leaves (White Crystal, a glutinous maize cultivar) using the cetyltrimethyl ammonium bromide method. Polymerase Chain Reaction ("PCR") was used to clone the maize GLK1 promoter (ZmG1; primers SEQ ID NOs: 9 and 10 in Table 1 below) and G2 promoter (ZmG2; primers SEQ ID NOs: 11 and 12) both containing the 5'-UTR region based on the sequences of ZmG1 (GRMZM2G026833) and ZmG2 (GRMZM2G087804) in the Ensembl plants database (found on the world wide web at plants.ensembl.org/index.html). Total RNA was extracted from maize embryonic leaves and used for cDNAs synthesis as described in Liu et al., PNAS 110:3979-3984 (2013). ZmG1 and ZmG2 cDNAs were cloned by PCR using specific primers shown in Table 1 below (ZmG1; SEQ ID NOs: 13 and 14: ZmG2; SEQ ID NOs: 15 and 16). The sequences of the promoters and full-length cDNAs of ZmG1 and ZmG2 were confirmed by sequencing.

TABLE 1

Primer Sequences

| Primer | Sequence (5' to 3') | SEQ ID NO: |
|---|---|---|
| G1 promoter_F | CCAACCCTGCATATCTTGC | 9 |
| G1 promoter_R | GGCGACACTGCAAGCATATC | 10 |
| G2 promoter_F | GCTATCTCCAACCACGGCTC | 11 |
| G2 promoter_R | CTTGCTGCCGCTGCTAGTAG | 12 |
| G1 cDNA_F | ATGCTTGCAGTGTCGCCGTC | 13 |
| G1 cDNA_R | TCATCCACAAGCTTGCGGCAC | 14 |
| G2 cDNA_F | ATGCTTGAGGTGTCGACGCTGCGC | 15 |
| G2 cDNA_R | TCATCCGGTGGCGCCGGTGG | 16 |
| Glp_F (XbaI) | CGTCTAGACCAACCGCTGCATATCTTG | 17 |
| Glp_R (BhI) | CAGGATCCGGCGACACTGCAAGCATA | 18 |
| G2p_mF (HdIII) | TGGCTTGGCACATGAAGCTT | 19 |
| G2p_R (BhI) | CAGGATCCACTTGCTGCCGCTGCTAG | 20 |
| G1_cDNA_F (BglII) | GGAGATCTATGCTTGCAGTGTCG | 21 |
| G1_cDNA_R (BglII) | GGAGATCTTCATCCACAAGCTTGCG | 22 |
| G2_cDNA_F (BglII) | GGAGATCTATGCTTGAGGTGTCG | 23 |
| G2_cDNA_F (BglII) | ATAGATCTTCATCCGGTGGCGCC | 24 |
| SP0 | TCGAGTTTCTCCATAATAATGTGTGA | 25 |
| SP1 | TAATGTGTGAGTAGTTCCCAGATA | 26 |
| SP2 | AATCCAGTACTAAAATCCAGATCC | 27 |
| AD1 | GTNCGASWCANAWGTT | 28 |
| AD2 | GWGNAGWANCASAGA | 29 |
| AD3 | NTCGASTWTSGWGTT | 30 |
| GT_F_G1 | CGATCGTGTTGGCACGTGATG | 31 |
| GT_R_G1 | TCGAAGAGTCAACCTTCGAGGTC | 32 |
| GT_F_G2 | GCCTTGGAGGAAGTAGAACAGC | 33 |
| GT_R_G2 | GTAGGTTTGGGAAATCTTTCAGC | 34 |
| GT_F_G1G2 | GTGACCGGAATCCCTCTCAAG | 35 |
| GT_R_G1G2 | GTTGCACTGTGTGTACTAGTC | 36 |

TABLE 1-continued

Primer Sequences

| Primer | Sequence (5' to 3') | SEQ ID NO: |
|---|---|---|
| G1p_F | CCAACCGCTGCATATCTTG | 37 |
| G1p_R | GGCGACACTGCAAGCATA | 38 |
| G2p_F | TGGCTTGGCACATGAAGCTT | 39 |
| G2p_R | CACTTGCTGCCGCTGCTAG | 40 |
| G1_mF | GTCGTTCTGGCACCATGCTTAC | 41 |
| G2_mF | CGCACAGAAAGCACCTGATGG | 42 |
| NOS_R | TCATCGCAAGACCGGCAACA | 43 |
| G1-F1 qPCR | GCACATAGGCGCCGTGGATCC | 44 |
| G1-R1 qPCR | TTACCGGCGGCTGCTACCTCG | 45 |
| G2-F qPCR | GACAAAGGTGTAGCAGTAGCCGCCGC | 46 |
| G2-R qPCR | CGTTGGAGTTCTTGCCCGCCGACTTC | 47 |
| OsGLK1-F qPCR | GATGCTGGCATGGAGGTCGTC | 48 |
| OsGLK1-R qPCR | TGCACACCTTCGCCTCCACTC | 49 |
| OsGLK2-F qPCR | GTGACGACGGAGGATTCCTCG | 50 |
| OsGLK2-R qPCR | CCGATGACGACGACGACGACG | 51 |
| OsFRD3_F_exon 1 | CGCGCTGTCCAAGGCCTATCTCT | 52 |
| OsFRD3_R_exon 1 | GCAACAGCATGGGGAGCATTGG | 53 |
| OsFRD3_F_exon 6 | GGCTTGGCATAACTGGAGCTGC | 54 |
| OsFRD3_R_exon 6-7 | AACTCAAAGCCCCCTGGGAGAG | 55 |
| OsFRD3_F_exon 7 | GGTGGCATGCTGTTAGGAAGAACCC | 56 |
| OsFRD3_R_exon 7 | GCCATAGCTGTTGGGCCTTGTCG | 57 |
| 17S rRNA_F | GATAACTCGACGGATCGCACGG | 58 |
| 17S rRNA_R | GCCTGCTGCCTTCCTTGGATGTG | 59 |
| OsActin_F | ATCCTTGTATGCTAGCGGTCGA | 60 |
| OsActin_R | ATCCAACCGGAGGATAGCATG | 61 |
| HptII_F | GACCTGATGCAGCTCTCGGAG | 62 |
| HptII_R | TGCTCCATACAAGCCAACCACG | 63 |

Construction of Transformation Vectors

Five constructs were made to express ZmG1 and ZmG2 genes in rice under the control of maize or constitutive promoters. The maize promoters and full-length cDNAs of these two genes were cloned by PCR and subcloned into the transformation vector pCAMBIA or Geteway (Invitrogen). The PCR fragments with compatible restriction sites were generated using specific primers (SEQ ID NOs: 17-24 in Table 1). The ZmG1 promoter and cDNA fragments were treated with XbaI/BamHI and BglII for both 5' and 3' ends, respectively, and the ZmG2 promoter and cDNA fragments were treated with HindIII/BamHI and BglII for both 5' and 3' ends, respectively. The ZmG1 promoter (2134 bp; SEQ ID NO: 1) fused to its cDNA (1428 bp; SEQ ID NO: 2) and ZmG2 promoter (1942 bp; SEQ ID NO: 4) fused to its cDNA (1386 bp; SEQ ID NO: 5) were separately ligated into an intermediate vector that contained a nopaline synthase terminator to obtain ZmG1pZmG1 and ZmG2p: ZmG2 fragments. All fragments in the intermediate vector were confirmed by restriction enzyme digestion analysis. Subsequently, the ZmG1pZmG1 fragment digested with EcoRI and the ZmG2p::ZmG2 fragment digested with HindIIII/EcoRI from the intermediate vector were ligated into the EcoRI and HindIIII/EcoRI sites of pCAMBIA1300 to generate the pZmG1::ZmG1 and pZmG2::ZmG2 constructs. In addition, the ZmG1p::ZmG1 fragment cut with EcoRI was cloned into the same restriction site of the ZmG2p::ZmG2 vector to generate the pZmG1ZmG1/pZmG2::ZmG2 construct.

To express maize G1 and G2 in rice under the control of a constitutive promoter, the Gateway entry clone containing the ZmG1 or ZmG2 cDNA was respectively transferred into the Gateway donor vector pCAMBIA1302 under the control of the maize ubiquitin promoter or pH2GW7 under the control of 35S promoter to generate the pZmUbi::ZmG1 and p35S::ZmG2 constructs.

The pZmUbi::ZmG1, p35S::ZmG2, pZmG1::ZmG1, pZmG2::ZmG2 and pZmG1::ZmG1/pZmG2::ZmG2 constructs containing the hygromycin phosphotransferase II gene for selection were each transfected separately into the *Agrobacterium tumefaciens* EHA105 strain via electroporation. All of the constructs are shown diagrammatically in FIG. 1.

Rice Transformation

Rice (*Oryza sativa* cultivar TNG67) callus induction, co-cultivation with *Agrobacterium*, hygromycin selection of transformed callus and plantlet regeneration were performed according to Yeh et al., 2015, Rice 8:36-48. All positive transgenic seedlings were transplanted into soil and cultivated in the greenhouse for molecular, physiological and anatomical analyses.

Determination of Transgene Insertion Location by Thermal Asymmetric Interlaced (TAIL)-PCR The conditions for TAIL-PCR were as described in Liu et al. (2013) and Møller et al. (2009). Genomic DNAs of TO transgenic plants was used as templates for three successive runs of PCR using a short arbitrary degenerate primer (AD; SEQ ID NOs: 28-30) and three specific nested primers (SP0; SEQ ID NO: 25, SP1; SEQ ID NO: 26 and SP2; SEQ ID NO: 27) to amplify T-DNA flanking genomic DNA regions. Tail-PCR products were purified and sequenced. Comparison of the PCR product sequences to the *Oryza sativa Japonica* Group DNA sequence in Ensemble Plants by BLAST (available on the World Wide Web at plants.ensembl.org/Multi/Tools/Blast?db=core) pinpointed the site of transgene insertion on a rice chromosome. The sequences identified were then used to evaluate the zygosity status of transgenic plants.

Screening of Homologous Transgenic Plants by Genotyping PCR

Genotyping primers were designed from the 3' and 5' end regions flanking the transgene insertion sites determined by Tail-PCR. Pairs of genome-specific primers (GT-F and GT-R; SEQ ID NOs: 31-36) were designed based on the chromosome DNA sequence across the putative insertion sites. In addition, transgene-specific SP2 and genome-specific primer GT-R were used for screening the presence of transgene insertion in transgenic plants. DNA was extracted from leaf tissues of T1 transgenic plants using Phire Plant Direct PCR Master Mix (Thermo Scientific) following the manual. PCR amplification was conducted with two primer sets (genome-specific GT-F and GT-R primers, and transgene-specific SP2 and genomic GT-R primers; Table 1) in a PCR reaction. The WT gave rise to only one PCR product from the genome-specific primer pair due to the absence of transgene. Heterozygous transgenic plants gave rise to two PCR products from amplifying (i) the non-disrupted strand of genome sequence by the genome-specific primer pair and (ii) the presence of one strand of transgene by SP2 and GT-R primers. In contrast, as both DNA strands were disrupted by the transgene insertion at a specific site, only one PCR product from the SP2 and GT-R primers was seen from homozygous transgenic plants. After screening, genomic DNA was isolated from young leaves of positive homozygous plants for further confirmation of the presence of maize GLK genes by PCR.

DNA Extraction and PCR

To detect maize GLK genes in transgenic rice plants, specific primers were used in PCR analysis (See Table 1, SEQ ID NOs: 37-43). Genomic DNA was isolated from young leaves of WT and representative transgenic rice plants by the CTAB method mentioned, supra. PCR amplification of maize GLK genes was performed in a thermal cycler under the following conditions: 94° C./5 min, 30 cycles of 94° C./30 sec, 58° C./30 sec and 72° C./30 sec, and a final extension at 72° C./5 min.

Southern Blot Analysis

Preparation of genomic DNA and Southern gel blot analysis were performed as previously described in Yeh et al. (2015). Genomic DNA was isolated from selected transgenic plants that had been confirmed for the presence of maize GLK genes by genomic PCR and digested with HindIII at 37° C. for 16-18 h, electrophoresed on a 1 agarose gel, and transferred to a nylon membrane for probe hybridization. Random primed DNA labeling with digoxigenin-dUTP probe was performed as directed in the DIG High Prime DNA Labeling and Detection Starter Kit II (Roche).

RNA Extraction and Quantitative Real-Time PCR (qRT-PCR)

Total RNA was isolated from leaves of WT and transgenic plants using TRIZOL reagent (Invitrogen) and purified by acid phenol-chloroform extraction. cDNA synthesis and qRT-PCR were performed as described in Yeh et al. Gene-specific primers for amplification of target genes (SEQ ID NOs: 44-57) and 17S gene (accession number X00755; SEQ ID NOs: 58 and 59) as an internal control for normalized expressing values are listed in Table 1.

Transcriptome Analysis

Total RNA was isolated from the shoots and roots of 4-days-old seedlings of WT, pZmG1::ZmG1, pZmG2"ZmG2 and pZmG1"ZmG1/pZmG2::ZmG2 transgenic plants using TRIZOL reagent (Invitrogen). Sample preparation and transcriptome analysis was accomplished using the methods of Liu et al. Sequencing reads were processed and mapped to the rice genome (IRGSP-1.0) using Tophat (version 2.0.10). Each read was aligned, allowing at most 10 hits. The expression level, i.e., reads per kilobase exon per million reads mapped ("RPKM") of each gene was estimated using Cufflinks (version 2.1.1). Genes with RPKM≥1 in at least one sample were considered "expressed" and selected for further analysis. To compare the expression levels of the selected genes across the shoot and root of WT, pZmG1::ZmG1, pZmG2::ZmG2 and pZmG1::ZmG1/pZmG2::ZmG2 transgenic plants, the upper quartile normalization procedure was adopted as described in Bullard et al., 2010, BMC Bioinform. 11:94. The non-parametric method of Tarazona et al. (2011, Genome Research 21:2213-2223) was employed to identify differentially expressed genes ("DEGs") between two samples and the q value (differential expression probability) in the method was set to be 0.740. The functional enrichment analysis was conducted with the background set of all expressed genes in this study. Fisher's exact test with false discovery rate ("FDR")<0.05 was applied with functional annotations from MapMan (see the World Wide Web at mapman.gabipd.org). For the functional classification of DEGs, the GO analysis was carried out by AgriGO V2 software with Fisher's exact test with FDR≤0.05 to get the GO annotations based on biological process.

GO Analysis of DEGs

To classify the biological function of DEGs, GO analysis was carried out using the AgriGO V2 software based on biological processes. The direct acyclic graph ("DAG") drawer is a visualization tool to illustrate the significant GO terms. The DAG, based on the nature of the GO structure, indicates the inter-relationships between terms. To investigate the effect of GLK genes for each transgenic rice, the up- and down-regulated DEGs from root and shoot were analyzed using the false discovery rate (FDR)≤0.05.

Protein Purification and Western Blot Analysis

Total soluble protein was extracted from newly mature leaves for SDS-PAGE and western immunodetection analyses, as described previously (See Dai et al., 1994, Planta 192:287-294 and Ku et al., 1999, Nat. Biotechnol. 17:76-80. Antibodies against maize Rubisco large subunit were prepared, as described by Ku et al. In addition, a partial 681 bp sequence of OsGLK1, which is consensus to the maize GLK genes (SEQ ID NO: 7), was cloned into a pET21b vector to produce recombinant protein for generation of anti-GLK antibodies. Antibodies raised against the rice/maize GLK partial peptide were purified by affinity chromatography (Yao-Hong Biotechnology Inc., Taiwan).

Chlorophyll Measurement and Rubisco Assay

Leaf segments from flag leaves or florets were collected and extracted in 96% ethanol. The chlorophyll content was calculated from the absorbances at 665 nm and 649 nm and expressed on the basis of leaf area or fresh weight. The activities of Rubisco were assayed as described previously. See Pyankov et al., 2000, Photosynth. Res. 63:69-84. Enzyme activities were based on chlorophyll content or leaf area.

Photosynthesis Measurement

The mid-sections of intact flag leaves on the major tillers of four-month-old rice plants grown in the greenhouse during flowering in the summer were used for $CO_2$ and $H_2O$ exchange measurements using a CIRAS2 portable photosynthesis system (PP system, Amesbury, MA). Measurements were conducted from 7:00 to 12:30 a.m. on sunny days and the conditions were 2000 μmol $m^{-2}s^{-1}$ photon flux density, 30° C. leaf temperature, 70% relative humidity and 415 ppm $CO_2$. The steady-state photosynthetic rate (Pn), stomatal conductance (Gs), intercellular $CO_2$ concentration (Ci) and transpiration rate (E) were recorded.

Transmission Electron Microscopy

Flag leaf samples (1 mm×2 mm) were fixed in 1% glutaraldehyde in 0.1 M phosphate-citrate buffer, pH 7.2 at 4° C. overnight. After rinsing in buffer three times for 20 min. each, the samples were postfixed in 1% $OsO_4$ in the same buffer for 2 h at room temperature and rinsed three times for 20 min. with changes of buffer. Samples were dehydrated in an acetone series, embedded in Spurr's resin, and sectioned with a Lecia Reichert Ultracut S or Lecia EM UC7 ultramicrotome. The ultra-thin sections (70-90 nm) were stained with 5% uranyl acetate/50% methanol and 0.4% lead citrate/0.1N NaOH. A FEI G2 Tecnai Spirit Twin transmission electron microscope at 80 KV was used for viewing and the images were recorded using a Gatan Orius CCD camera.

Agronomic Traits Studies

WT and GLK transgenic rice plants were cultivated in five-liter pots (one plant/pot) in a greenhouse between March and August under natural sunlight conditions. Plants were watered daily and fertilized weekly. Upon maturation, total aboveground biomass, total panicle number, 1000-grain weight, and total grain weight per plant were analyzed after drying for two days at 43° C. for seeds and 60° C. for shoots.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A transgenic rice plant, comprising in its genome a recombinant DNA construct that contains a first nucleic acid having a sequence of a first Golden 2-like transcription factor (GLK) gene operably linked to its natural promoter and 5' untranslated region (5'UTR), and a second nucleic acid having a sequence of a second GLK gene operably linked to its natural promoter and 5'UTR, wherein the first GLK gene is *Zea mays* GLK1, the second GLK gene is *Zea mays* GLK2, both the first GLK gene and the second GLK gene are expressed in the transgenic rice plant, and the transgenic rice plant exhibits at least a 50% increase in shoot biomass and grain yield, as compared to an untransformed wild-type rice plant.

2. The transgenic rice plant of claim 1, wherein the first nucleic acid sequence includes a first coding sequence that encodes a protein having the amino acid sequence of SEQ ID NO: 3 and the second nucleic acid sequence includes a second coding sequence that encodes a protein having the amino acid sequence of SEQ ID NO: 6.

3. The transgenic rice plant of claim 2, wherein the natural promoter and 5'UTR of the first GLK gene has the sequence of SEQ ID NO: 1 and the natural promoter and 5'UTR of the second GLK gene has the sequence of SEQ ID NO: 4.

4. The transgenic rice plant of claim 2, wherein the first coding sequence is SEQ ID NO: 2 and the second coding sequence is SEQ ID NO: 5.

5. The transgenic rice plant of claim 1, wherein the grain yield of the transgenic rice plant is 50% to 95% higher, as compared to the untransformed wild-type rice plant.

6. A method of producing a transgenic rice plant, the method comprising:
   introducing into a host rice plant a recombinant DNA construct that contains a first nucleic acid sequence including a first Golden 2-like transcription factor (GLK) gene operably linked to its natural promoter and 5'UTR, a second nucleic acid sequence including a second GLK gene operably linked to its natural promoter and 5'UTR, the first GLK gene being *Zea mays* GLK1 and the second GLK gene being *Zea mays* GLK2; and
   identifying a transgenic rice plant that exhibits at least a 50% increase in shoot biomass and grain yield, as compared to an untransformed wild-type rice plant.

7. The method of claim 6, wherein the first nucleic acid sequence includes a first coding sequence that encodes a protein having the amino acid sequence of SEQ ID NO: 3 and the second nucleic acid sequence includes a second coding sequence that encodes a protein having the amino acid sequence of SEQ ID NO: 6.

8. The method of claim 7, wherein the natural promoter and 5'UTR of the first GLK gene has the sequence of SEQ ID NO: 1 and the natural promoter and 5'UTR of the second GLK gene has the sequence of SEQ ID NO: 4.

9. The method of claim 6, wherein the first coding sequence is SEQ ID NO: 2 and the second coding sequence is SEQ ID NO: 5.

10. The method of claim 6, wherein the grain yield of the transgenic rice plant is 50% to 95% higher, as compared to the untransformed wild-type rice plant.

11. The method of claim 6, wherein the shoot biomass of the transgenic rice plant is 65% to 106% higher, as compared to the untransformed wild-type rice plant.

12. A recombinant DNA construct, comprising a first nucleic acid sequence that includes a first Golden 2-like transcription factor (GLK) gene operably linked to its natural promoter and 5'UTR, and a second nucleic acid sequence that includes a second GLK gene operably linked to its natural promoter and 5'UTR, wherein the first GLK gene is *Zea mays* GLK1 and the second GLK gene is *Zea mays* GLK2.

13. The recombinant DNA construct of claim 12, wherein the first nucleic acid sequence includes a first coding sequence that encodes a protein having the amino acid sequence of SEQ ID NO: 3 and the second nucleic acid sequence includes a second coding sequence that encodes a protein having the amino acid sequence of SEQ ID NO: 6.

14. The recombinant DNA construct of claim 13, wherein the natural promoter and 5'UTR of the first GLK gene has the sequence of SEQ ID NO: 1 and the natural promoter and 5'UTR of the second GLK gene has the sequence of SEQ ID NO: 4.

15. The recombinant DNA construct of claim 13, wherein the first coding sequence is SEQ ID NO: 2 and the second coding sequence is SEQ ID NO: 5.

* * * * *